(12) United States Patent
Marmion et al.

(10) Patent No.: US 8,901,337 B2
(45) Date of Patent: Dec. 2, 2014

(54) METAL COMPLEXES HAVING DUAL HISTONE DEACETYLASE INHIBITORY AND DNA-BINDING ACTIVITY

(75) Inventors: Celine Josephine Marmion, Wicklow (IE); Darren Griffith, Dublin (IE)

(73) Assignee: Royal College of Surgeons in Ireland, Dublin (IE)

( * ) Notice: Subject to any disclaimer, the term of this patent is extended or adjusted under 35 U.S.C. 154(b) by 271 days.

(21) Appl. No.: 13/384,088

(22) PCT Filed: Jul. 13, 2010

(86) PCT No.: PCT/EP2010/060089
§ 371 (c)(1),
(2), (4) Date: Mar. 28, 2012

(87) PCT Pub. No.: WO2011/006908
PCT Pub. Date: Jan. 20, 2011

(65) Prior Publication Data
US 2012/0190874 A1    Jul. 26, 2012

Related U.S. Application Data

(60) Provisional application No. 61/225,952, filed on Jul. 16, 2009.

(30) Foreign Application Priority Data

Jul. 16, 2009 (EP) .................................... 09165715

(51) Int. Cl.
*C07F 15/00* (2006.01)
*C07C 259/06* (2006.01)
*C07C 311/21* (2006.01)

(52) U.S. Cl.
CPC ........... *C07F 15/0093* (2013.01); *C07C 311/21* (2013.01); *C07C 259/06* (2013.01)
USPC .............................. 556/137; 556/136; 562/623

(58) Field of Classification Search
USPC .................................. 556/136, 137; 562/623
See application file for complete search history.

(56) References Cited

U.S. PATENT DOCUMENTS 8,304,451 B2 * 11/2012 Mazitschek et al. .......... 514/452
2005/0119305 A1    6/2005 Naka et al.

FOREIGN PATENT DOCUMENTS

WO          00/74681          12/2000
WO      2007/056243           5/2007
WO  WO 2007/058992 A2 *       5/2007

OTHER PUBLICATIONS

Stoermer, D., et al. "Symthesis and biological evaluation of hydroxamate-based inhibito of glutamate carbosypeptidase II", Bioorganic & Medicinal Chemistry Letters, 2003, pp. 2097-2100.

(Continued)

*Primary Examiner* — Porfirio Nazario Gonzalez
(74) *Attorney, Agent, or Firm* — Cesari and McKenna, LLP

(57) ABSTRACT

Compounds comprising a metal complex having the structure $[X-Y-Z-M^{n+}]^{P+} \cdot B$ are disclosed in which X is a histone deacetylase inhibitor, $M^{n+}$ is a DNA-binding heavy metal ion, Y is an aliphatic or aromatic spacer or is absent, and Z is a mono- or bi-dentate or chelating donor linker, or a bridging linker, P+ designates the charge on the complex ion, which may be positive, negative or absent and B is a counterion or is absent. The linker Z is labile and its metal complex $X-Y-Z-M^{n+}$ is capable of being hydrolysed in-vivo. The compounds find application in the treatment of cancer.

17 Claims, 19 Drawing Sheets

(56) References Cited

OTHER PUBLICATIONS

Uttamchandani, M., et al. "Inhibitor fingerprinting of matrix metalloproteases using a combinatorial peptide hydroxamate library" The Journal of the American Chemical Society, 2007, pp. 7848-7858.

Salmi-Smail, C., et al. "Modified cap group suberoylanilide hydroxamic acid histone deacetylase inhibitor derivatives reveal improved selective antileukemic activity", Journal of Medicinal Chemistry, Mar. 10, 2010, pp. 3038-3047.

Griffith, D., et al. "A novel anti-cancer bifunctional platinum drug candidate with dual DNA binding and histone deacetylase inhibitory activity", Chemical Communications, Oct. 12, 2010, pp. 6735-6737.

Xie, J. et al. "Inhibitors of the enkephalin degrading enzymes, Modulation of activity of hydroxamate containing compounds by modifications of the C-terminal residue", International Journal of Peptide & Protein Research, 1989, abstract only.

\* cited by examiner

Cisplatin        Carboplatin        Oxaliplatin

- DNA Ladder
- DNA (30 µM) + 0 µM
- DNA (30 µM) + 1.0 µM
- DNA (30 µM) + 10 µM
- DNA (30 µM) + 20 µM
- DNA (30 µM) + 30 µM
- DNA (30 µM) + 40 µM
- DNA (30 µM) + 50 µM
- DNA (30 µM) + 60 µM
- DNA (30 µM) + 70 µM
- DNA (30 µM) + 80 µM
- DNA (30 µM) + 90 µM
- DNA (30 µM) + 100 µM
- DNA (30 µM) + 0 µM
- DNA (30 µM) + 30 µM Cis
- DNA (30 µM) + 40 µM Cis
- DNA Ladder Control 0.5 % DMF Cisplatin at 1.3 μM (IC$_{50}$)

Cisplatin at 5.0 μM (IC$_{75}$)

cis-[Pt$^{II}$(NH$_3$)$_2$(malBel$_{-2H}$)]
at 7.6 μM (IC$_{50}$)

cis-[Pt$^{II}$(NH$_3$)$_2$(malBel$_{-2H}$)]
at 12.0 μM (IC$_{75}$)

Control 0.5 % DMF

Cisplatin at 9.7 μM (IC$_{50}$)

Cisplatin at 18.0 μM (IC$_{75}$)

cis-[Pt$^{II}$(NH$_3$)$_2$(malBel$_{-2H}$)]
at 11.7 μM (IC$_{50}$)

cis-[Pt$^{II}$(NH$_3$)$_2$(malBel$_{-2H}$)]
at 25.0 μM (IC$_{75}$)

Control 0.5 % DMF

Cisplatin at 1.3 μM (IC$_{50}$)

Cisplatin at 5.0 μM (IC$_{75}$)

cis-[Pt$^{II}$(NH$_3$)$_2$(malBel$_{-2H}$)]
at 7.6 μM (IC$_{50}$)

cis-[Pt$^{II}$(NH$_3$)$_2$(malBel$_{-2H}$)]
at 12.0 μM (IC$_{75}$)

METAL COMPLEXES HAVING DUAL HISTONE DEACETYLASE INHIBITORY AND DNA-BINDING ACTIVITY

RELATED APPLICATIONS

This application is a national stage filing under 35 U.S.C. §371 of international application PCT/EP2010/060089, filed Jul. 13, 2010, and claims priority under 35 U.S.C. 119(e) to U.S. Provisional Patent Application No. 61/225,952, filed Jul. 16, 2009, and European Patent Application 09165715.5, filed Jul. 16, 2009, the disclosures of which are incorporated herein by reference.

INTRODUCTION

The invention relates to metal complexes having dual histone deacetylase inhibitory and DNA-binding activity, and uses thereof in the treatment of cancer. The invention also provides intermediate compounds useful in preparing the metal complexes of the invention.

Nearly 50% of all anti-cancer therapies are platinum (Pt)-based,[1] yet surprisingly to date only three Pt drugs have been approved for worldwide clinical use, namely cisplatin, carboplatin and oxaliplatin, FIG. 1 (comparative).[2] The cytotoxicity of Pt drugs is attributed to their ability to bind DNA and induce apoptosis. Despite their success, the widespread application and efficacy of classical Pt drugs is hindered by toxic side effects, their limited activity against many common human cancers and their susceptibility to intrinsic/acquired drug resistance.[2] Some of these drawbacks, which undermine their curative potential against many malignancies, may be due to their lack of selectivity for the cell nucleus resulting in reduced cellular accumulation because of increased detoxification by cytoplasmic glutathione and/or metallothioneins or their reactions with other biomolecules such as proteins and phospholipids. Once DNA binding has occurred, resistance mechanisms include increased DNA repair of adducts and an ability to tolerate greater levels of DNA damage.[2] Alternative strategies are therefore required in an attempt to overcome these drawbacks such as developing a new class of chemotherapeutic with greater selectivity for cancer cells over normal cells and with a different mechanism of action to commercially available Pt drugs.

The cytotoxicity of Pt-drugs such as cisplatin, cis-[Pt$^{II}$(NH$_3$)$_2$Cl$_2$], is attributed to their ability to undergo hydrolysis upon cell entry, forming hydrated species such as [Pt$^{II}$(NH$_3$)$_2$(H$_2$O)$_2$]$^{2+}$ which bind to DNA nucleobases (of which 60-65% consists of 1,2-intrastrand GpG cross-links between two adjacent guanines), distorting the DNA helix and interfering with DNA processes such as transcription and replication. These distortions are thought to trigger apoptosis.[2] However, Pt drugs react indiscriminately in the body giving rise to many of the drawbacks associated with their use.

There is therefore an urgent need to develop novel therapeutics that overcome these drawbacks. As such, the search for new molecular targets beyond DNA which may present unique opportunities for therapeutic exploitation, is currently the subject of intense investigation. Chromatin, a complex structure that plays a key role as an epigenetic regulator of gene expression, is one such target. Its fundamental repeating unit, the nucleosome, consists of core histones around which DNA coils FIG. 2 (comparative). Some histone residues protrude the nucleosome and are subject to many enzyme-catalysed post-translational modifications including methylation and acetylation. Acetylation is controlled by two enzymes, histone acetyltransferases (HAT's) and histone deacetylases (HDAC's), which work in harmony to acetylate and deacetylate core histone lysine residues respectively. Acetylation leads to an open chromatin structure that upregulates transcription whereas deacetylation leads to a condensed structure and transcriptional repression.[3, 4] Inhibition of HAT's or HDAC's can therefore dramatically affect chromatin structure and reprogram transcription and in fact a range of structurally diverse HDAC inhibitors (HDACi's) have already been shown to cause cell cycle arrest, differentiation and/or apoptosis of tumour cells, FIG. 3.[5, 6] Several of these are now undergoing clinical trials.[7] Suberoylanilide hydroxamic acid (SAHA), FIG. 4, is the first FDA-approved HDACi to enter the clinic as an orally active treatment for advanced cutaneous T-cell lymphoma.

STATEMENTS OF INVENTION

HDACi's such as SAHA have been shown to have preferential selectivity for cancer cells over normal cells[3, 8] and have also been shown to synergistically enhance the anticancer activity of many chemotherapeutics.[9, 10] Since Pt drugs react indiscriminately in the body giving rise to many of the drawbacks associated with their use, by tethering a HDAC inhibitor to Pt, a synergistic (or at least an additive) effect results whereby the presence of the inhibitor, with its known affinity for tumour cells, confers selectivity to the drug and deliver the complex containing the potent chemotherapeutic Pt (DNA binding agent) and the HDAC inhibitor to its cancer target (cell nucleus rich in HDAC enzymes). These compounds typically have a mechanism of action different to classical Pt drugs due to their dual DNA binding and HDAC inhibitory properties and are typically active against (i) a broader spectrum of human cancer cells relative to classical Pt drugs and (ii) human malignancies that have acquired resistance to conventional Pt-based therapies. Because of enhanced selectivity for cancer cells as compared to normal cells, they are suitably less toxic, thus reducing the severe side effects associated with classical Pt drugs.

Broadly, the invention relates to metal complexes having dual histone deacetylase inhibitory activity and DNA binding activity. The metal complexes of the invention comprise a first structure, generally designated X, providing HDAC inhibitory activity and suitably having a terminal HDAC active site inhibiting group (for example, a terminal hydroxamate or benzamide group), coordinated to a DNA-binding heavy metal ion M$^{n+}$ by means of a linker Z, and optionally a spacer group Y. Typically, the metal complexes of the invention have the general formula:

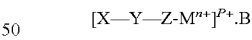

[X—Y—Z-M$^{n+}$]$^{P+}$.B in which:
X is a HDAC inhibitor having a terminal HDAC active site inhibiting group;
Y is a spacer group or is absent;
Z is a linker;
M$^{n+}$ is a DNA-binding heavy metal ion selected from platinum, palladium, ruthenium, osmium, gold, iron and copper, in which the heavy metal ion is coordinated to one or more ligands to complete its coordination sphere;
P+ designates the charge on the complex ion, which may be positive, negative or absent; and
B is a counterion or is absent.

The linker Z is suitably a monodentate, bidentate or chelating oxygen donor group(s), or a bridging linker group. Suitable examples include mono- or multi-dentate hydroxyl or carboxylate groups, and may take the form of a single substituent (for example an aromatic or aliphatic dicarboxylate)

or two substituents (for example, two hydroxyl, two carboxylate, or one hydroxyl and one carboxylate substituent). In either case, Y may be absent and the linker Z comprises one or two substituents appended to the HDAC inhibitor X, generally at or adjacent to a protein recognition domain of the HDAC inhibitor. In most cases, the linker Z is designed such that it is labile and when coordinated to a DNA-binding metal ion, the corresponding complex is susceptible to hydrolysis in vivo, thereby releasing the HDAC inhibitor and leaving the metal ion free to bind DNA. However, in other cases, the linker is not labile, wherein the compound is capable of providing HDAC inhibitory activity and DNA binding while intact.

The invention also provides an intermediate compound that is capable of coordinating a DNA-binding heavy metal ion and comprising a HDAC inhibitor X (having a terminal HDAC active site inhibiting group) bound to a linker Z, optionally via a spacer group Y, wherein the linker group is capable of coordinating the DNA-binding metal ion. As above, the linker group is preferably labile to hydrolysis in vivo to release the DNA-binding metal ion. The compounds of the invention have numerous advantages. First, as the HDAC inhibitor is capable of targeting the compound to cancer cells, this reduces the cytotoxicity to non-cancer cells associated with conventional DNA-binding drugs such as CISPLATIN and CARBOPLATIN (FIG. 1—comparative). Secondly, the dual activity of the compounds overcomes the problems of resistance to DNA-binding drugs associated with certain cancers.

The metal complexes and intermediates of the invention may include many classes of HDAC inhibitors, such as the hydroxamate and benzamide-type inhibitors described in Cancer Letters 280 (2009) 233-241, and the HDAC inhibitors described in the Journal of Hematology & Oncology 2009, 2:22. The HDAC inhibitor X is preferably a hydroxamate-type inhibitor, such as those described in U.S. Pat. No. 6,087,367, U.S. Pat. No. 6,552,065, and U.S. Pat. No. 6,888,027, which have a terminal hydroxamate group which is the active site inhibiting group. Preferred hydroxamate-type HDAC inhibitors are SAHA (Vorinostat), Panobinostat, or Belinostat. The HDAC inhibitor X may alternatively be benzamide-type inhibitor, which have a terminal benzamide group which is the active site inhibiting group.

The linker Z may be any chemical group or groups that is/are capable of complexing a DNA-binding metal ion. Typically, the linker Z also must be capable of being hydrolysed in-vivo. Particularly suitable linkers are mono- and multi-dentate, or chelating, oxygen donor groups, such as hydroxyl or carboxylate groups. Preferred DNA-binding metal ions are platinum, ruthenium, palladium, osmium, gold, iron and copper.

Intermediate Compounds

The invention also provides intermediate compounds useful in preparing the metal complexes of the invention and comprising a HDAC inhibitor having a terminal active site inhibiting group (i.e. a group, such as hydroxamate or benzamide, which in use inhibits the active site of the histone deacetylase enzyme) and a terminal linker Z (generally appended at or adjacent to a protein recognition domain of the HDAC inhibitor molecule) which is capable of coordinating a DNA-binding heavy metal ion. When derivatised with the linker Z, the intermediate compound generally comprises mono-, bi-dentate, chelating oxygen donor, or bridging, ligands. Preferred examples include bidentate O,O' HDAC inhibitor ligands, a monodentate O HDAC inhibitor ligand, a chelating oxygen donor ligand, or a bridging ligand.

Thus, in a first aspect of the invention, there is provided a compound of general formula I:

X—Y—Z    (I)

or a pharmaceutically acceptable salt thereof, in which:
X is a histone deacetylase (HDAC) inhibitor having a terminal HDAC active site inhibiting group;
Y is an aliphatic or aromatic spacer or is absent; and
Z is a linker capable of coordinating a DNA-binding metal ion, typically selected from platinum, palladium, ruthenium, osmium, gold, iron and copper (hereafter "Intermediate Compound").

Preferably, X is a HDAC inhibitor having a terminal hydroxamate or benzamide group.

Preferably, Z is one or more mono-, bi-dentate, or chelating, oxygen donor groups, for example mono-dentate or bi-dentate hydroxyl or carboxylate groups. Examples of suitable oxygen mono- or multi-dentate or chelating donor ligands include:

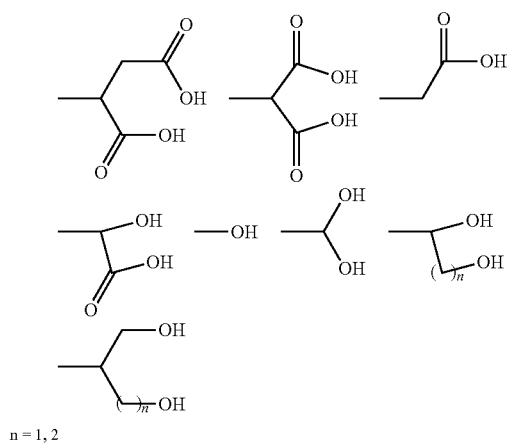

n = 1, 2

Thus, the Intermediate Compound of the invention may have a structure selected from the group consisting of:

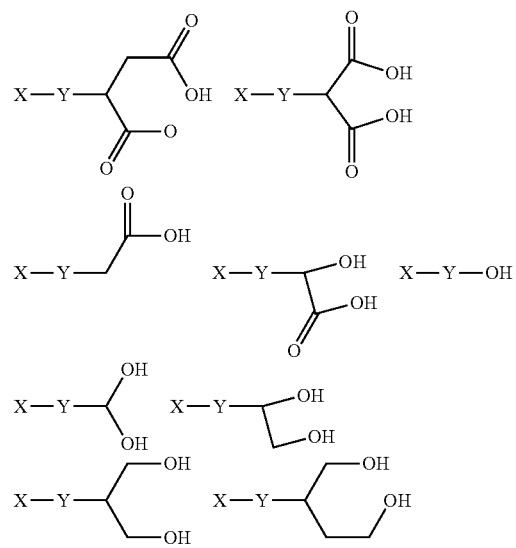

In one embodiment, the HDAC inhibitor X has a general formula II:

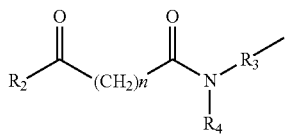
(II)

in which:

R$_3$ and R$_4$ are each, independently, a hydrogen, hydroxyl, a substituted or unsubstituted, branched or unbranched alkyl, for example a C$_1$-C$_6$ alkyl, alkenyl, cycloalkyl, for example a C$_4$-C$_9$ cycloalkyl, aryl, acyl, heteroaryl, arylalkyl, heteroarylalkyl, aryloxy, alkyloxy, arylalkyloxy, aromatic polycycles, non-aromatic polycycles, mixed aryl and non-aryl polycycles, polyheteroaryl, non-aromatic polyheterocycles, and mixed aryl and non-aryl polyheterocycles, or a pyridine group.

R$_2$ is a hydroxylamino, hydroxyl, amino, alkylamino, dialkylamino, or alkoxy group; and n is an integer from 5 to 8.

Typically, R$_2$ is a hydroxylamino, hydroxyl, amino, methylamino, dimethylamino, or a methoxy group. Ideally, R$_2$ is a hydroxylamino group. Suitably, R$_4$ is a hydrogen atom.

In a preferred embodiment of the invention, R$_3$ is a substituted or unsubstituted phenyl group. Suitably, the phenyl group is substituted with a halogen, for example, a chloro, bromo, fluoro, or iodo group, a methyl, cyano, nitro, trifluoromethyl, amino, methylcyano, sulphonate, or aminocarbonyl group. In another embodiment, R$_3$ is selected from the group consisting of methoxy, cyclohexyl, hydroxyl, benzyloxy, and pyridine.

HDAC inhibitors of general formula II are described in U.S. Pat. No. 6,087,367, especially the specific structures described in Table 1. The complete contents of U.S. Pat. No. 6,087,367 are incorporated herein by reference.

In one embodiment, the Intermediate Compound of the invention has the structure III:

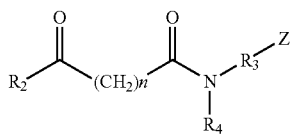
(III)

in which R$_2$, R$_3$, R$_4$, n, and Z are as defined above.

In a preferred embodiment, R$_3$ is a phenyl group and Z comprises one or more hydroxyl or carboxylate substituents. Typically. R$_3$—Z is selected from the group consisting of:

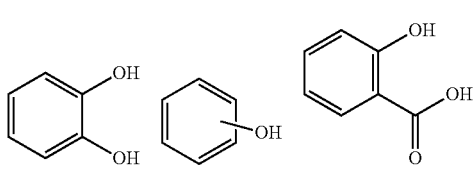

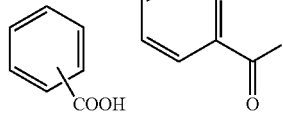

Thus, in one embodiment, the linker group Z may comprise one or two substituents appended to the HDAC inhibitor (forming, for example, a bidentate O,O' ligand or a monodentate O ligand, or a chelating oxygen donor ligand, or a bridging ligand). Thus, the Intermediate Compounds of the invention are in one embodiment selected from the group consisting of:

The five compounds illustrated above are Intermediate Compounds suitable for preparing metal complexes having a DNA-binding metal ion tethered to a hydroxamate-type HDAC inhibitor.

In another embodiment, the HDAC inhibitor X is a hydroxamate-type HDAC inhibitor having a general formula IV:

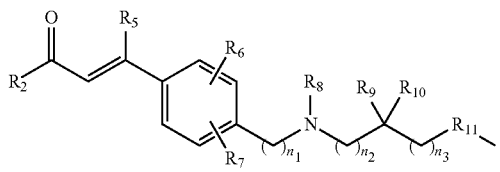

in which:

R$_2$ is as defined above;

R$_5$ is H, halo, or a straight chain C$_1$-C$_6$ alkyl;

R$_6$ and R$_7$ are the same or different and independently selected from H, halo, C1 to C$_4$ alkyl, such as CH$_3$ and CF$_3$, NO$_2$, C(O)R$_5$, OR$_{12}$, SR$_{12}$, CN, NR$_{13}$R$_{14}$;

R8 is selected from H, C$_1$ to C$_{10}$ alkyl, C$_4$ to C$_9$ cycloalkyl, C$_4$ to C$_9$ heterocycloalkyl, C$_4$ to C$_9$ heterocycloalkylalkyl, cycloalkylalkyl, aryl, heteroaryl, arylalkyl, heteroarylalkyl, —(CH$_2$)$_n$C(O)R$_6$, —(CH$_2$)$_n$O(O)R$_6$, amino acyl, and HON—C(O)—CH=C(R$_1$)-aryl-alkyl;

R$_9$ and R$_{10}$ are the same or different and independently H, C$_1$-C$_6$ alkyl, acyl or acylamino, or R$_3$ and R$_4$ together with the carbon to which they are bound represent C=O, C=S, or R$_8$ together with the nitrogen to which it is bound and R$_9$ together with the carbon to which it is bound can form a C$_4$-C$_9$ heterocycloalkyl, a heteroaryl, a polyheteroaryl, a non-aromatic polyheterocycle, or a mixed aryl and non-aryl polyheterocycle ring;

R$_{11}$ is selected from H, C$_1$-C$_6$ alkyl, C$_4$-C$_9$ cycloalkyl, C$_4$-C$_9$ heterocycloalkyl, acyl, aryl, heteroaryl, arylalkyl, heteroarylalkyl, aromatic polycycles, non-aromatic polycycles, mixed aryl and non-aryl polycycles, polyheteroaryl, non-aromatic polyheterocycles, and mixed aryl and non-aryl polyheterocycles;

R$_{12}$ is selected from C$_1$-C$_4$ alkyl, for example CH$_3$ and CF$_3$, C(O)-alkyl, for example C(O)CH$_3$ and C(O)CF$_3$;

R$_{13}$ and R$_{14}$ are the same or different and independently selected from H, C$_1$-C$_4$ alkyl, and —C(O)-alkyl; and n$_1$, n$_2$ and n$_3$ are the same or different and independently selected from 0-6, when n$_1$ is 1-6, each carbon atom can be optionally and independently substituted with R$_9$ and/or R$_{10}$.

Compounds of general formula IV are describes in U.S. Pat. No. 6,552,056, especially the generic structures described on column 3 to 14, and the specific structure numbers 1 to 265 described on columns 23 to 142. The complete contents of U.S. Pat. No. 6,552,056 are incorporated herein by reference.

The hydroxamate-type HDAC inhibitor X of general formula IV preferably has a structure selected from the group:

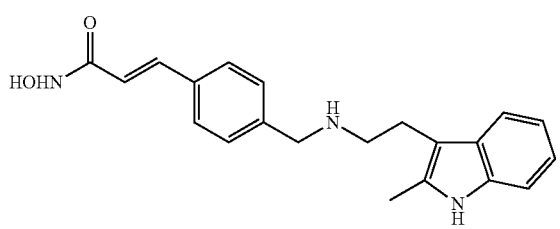

Panobinostat: LBH589

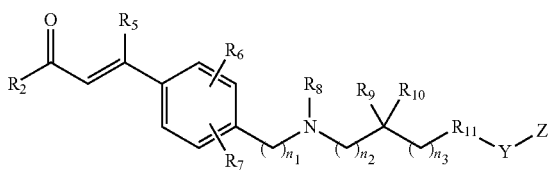

LAQ-824

The hydroxamate-type HDAC inhibitors of general formula IV may be derivatised with a linker Z that is capable of coordinating a DNA-binding metal ion and optionally a spacer group Y to provide Intermediate Compounds of general formula V:

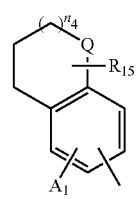

in which:

R$_2$, R$_5$, R$_6$, R$_7$, R$_8$, R$_9$, R$_{10}$, Y, Z and n$_1$ to n$_3$ are as defined above;

n$_4$ is 0, 1 or 2;

R$_{11}$ is

R$_{15}$ is selected from H, halo, C1 to C$_6$ alkyl, C$_3$ to C$_7$ cycloalkyl, aryl, for example unsubstituted phenyl or phenyl substituted by 4-OCH$_3$ or 4-CF$_3$, or heteroaryl, such as 2-furanyl, 2-thiophenyl, or 2-, 3- or 4-pyridyl;

Q is O, S, or NR$_{16}$, where R$_{16}$ is selected from H, C1-C$_6$ alkyl, C$_1$-C$_6$alkyl-C$_3$-C$_9$cycloalkyl, aryl, heteroaryl, arylalkyl, heteroarylalkyl, acyl, or sulfonyl; and A$_1$ is 1, 2 or 3 substituents which are independently H, C$_1$-C$_6$ alkyl, —OR$_{12}$, halo, alkylamino, aminoalkyl, or heteroarylalkyl.

In one embodiment, Y is absent, R$_{11}$ is as defined above, and R$_{11}$—Z has a structure selected from the group consisting of:

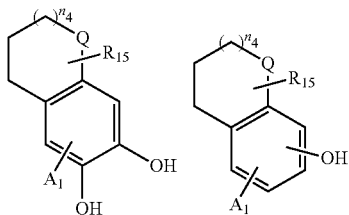

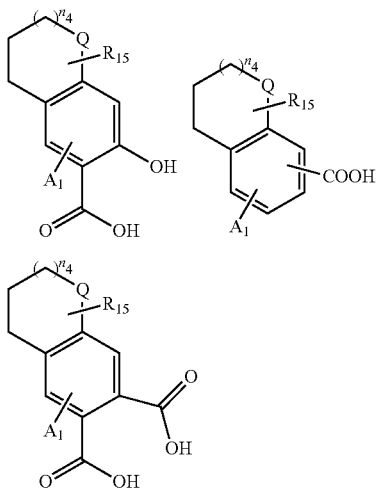

In another embodiment of the invention, —R$_{11}$—Z has a structure

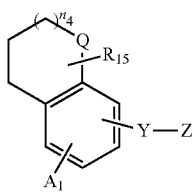

in which Y and Z are as defined previously.

In another embodiment, the HDAC inhibitor X is a hydroxamate-type HDAC inhibitor having a general formula VI:

R$_{17}$-Q$_2$-J-Q$_1$-A-     (VI)

in which:

A is an aryl group;

Q$_1$ is a covalent bond or an aryl leader group;

J is a sulfonamide linkage selected from

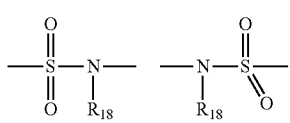

where R$_{18}$ is a sulfonamide substituent;

Q$_2$ is an acid leader group; and

R17 is a terminal hydroxamate group, with the proviso that if J is

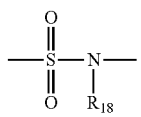

then Q$_1$ is an aryl leader group.

The hydroxamate-type HDAC inhibitor X of general formula VI preferably has a structure:

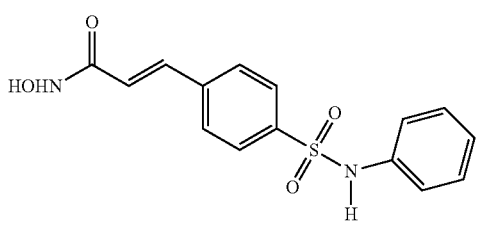

Belinostat: PXD-101

Compound of general formula VI are described in WO02/30879, especially the generic compound number 4, 12, 15 on pages 17, 56 and 57, respectively, and the specific structure numbers 1 to 125 described on pages 58-72. The complete contents of WO02/30879 are incorporated herein by reference.

In another embodiment, the HDAC inhibitor X is a benzamide-type HDAC inhibitor having a terminal benzamide group which is an active site inhibiting group. Typically, the benzamide-type HDAC inhibitor has a general structure shown in Formula 1 of EP0847992A1 (page 3), or a specific structure selected from the compound 1 to 240 shown in Tables 1(1) to 1(23) of EP0847992A1. In one preferred embodiment, the benzamide HDAC inhibitor is selected from the group consisting of:

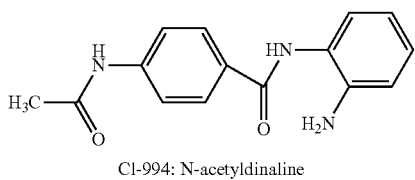

CI-994: N-acetyldinaline

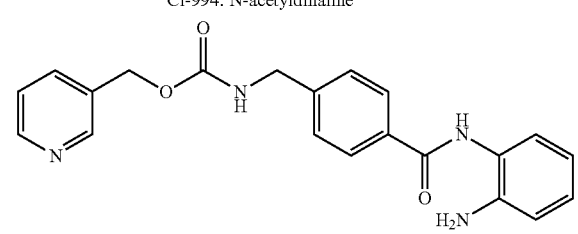

MS-275

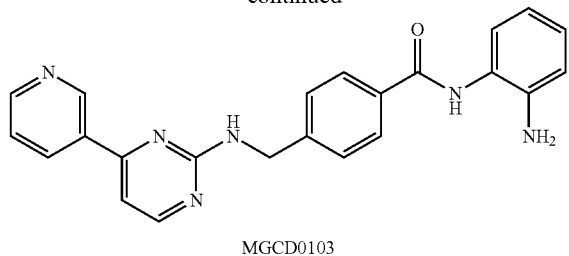

MGCD0103

Metal Complexes

The invention also relates to an Intermediate Compound of the invention coordinated to a heavy metal ion $M^{n+}$ via the linker Z, and typically capable of dual DNA binding and HDAC inhibitory activity (hereafter "Metal Complex").

Thus, the Metal Complex of the invention comprises a first structure, generally designated X, providing HDAC inhibitory activity and suitably having a terminal HDAC active site inhibiting group (for example, a terminal hydroxamate or benzamide group), coordinated to a DNA-binding heavy metal ion M by means of a linker group Z, and optionally a spacer group Y:

$$[X—Y—Z-M^{n+}]^{P+}.B$$

in which:
X is HDAC inhibitor having a terminal HDAC active site inhibiting group;
Y is a spacer group or is absent;
Z is a mono-dentate, bi-dentate, chelating, or bridging, oxygen donor linker group;
$M^{n+}$ is a DNA-binding heavy metal ion selected from platinum, palladium, ruthenium, osmium, gold, iron and copper, in which the heavy metal ion is coordinated to one or more ligands to complete its coordination sphere;
P+ is the charge on the complex ion which may be positive, negative or absent; and
B is a counterion or is absent.

Examples of suitable counterions will be well known to the person skilled in the art, and include: acid addition salts such as the hydrochlorides, hydrobromides, phosphates, sulphates, hydrogen sulphates, alkylsulphates, arylsulphonates, acetates, benzoates, citrates, maleates, fumarates, succinates, lactates, and tartrates; alkali metal cations such as Na, K, and Li; alkali earth metal salts such as Mg or Ca; or organic amine salts. For ease of reference, the Metal Complex formulae provided hereafter do not illustrate a counterion, however it will be appreciated that in cases where the complex ion $[X—Y—Z-M^{n+}]$ has a positive or negative charge, that the metal complex will comprise a suitable counterion.

Thus, in a second aspect, the invention provides a Metal Complex of general formula VII, VIII or IX:

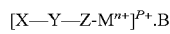

(VII)

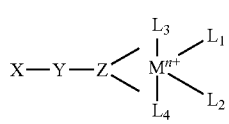

(VIII)

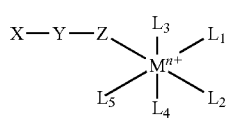

(IX)

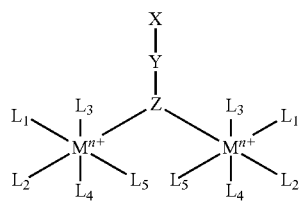

in which:
X, Y, Z and $M^{n+}$ are as defined above; and
$L_1$ to $L_5$ are typically each, independently, selected from the group consisting of: ammonia; a primary amine; a secondary amine; a non-planar heterocyclic aliphatic amine or a heterocyclic aromatic amine (such as pyridine, imidazole, indazole, bipyridine, phenanthroline and derivatives); a sulphur donor ligand such as dimethyl sulfoxide; a phosphorous donor ligand such as a phosphine; a halogen; an oxygen donor ligand such as water or hydroxyl or hydroxide or methoxy or acetate; a multidentate chelating ligand formed between two or more of $L_1$-$L_5$; or a mono- or bi-dendate or bridging X—Y—Z.

Representative structures of mono- or bi-dendate or bridging X—Y—Z metal complexes are shown in FIG. 5. The presence or absence of ligands $L_1$ to $L_5$ is determined by the oxidation state and geometry of the DNA-binding metal ion $M^{n+}$.

Thus, where Z is a bidentate O,O' linker and $M^{n+}$ is square planar $Pt^{2+}$ or $Pd^{2+}$ in cis geometry, then $L_3$ and $L_4$ are absent and $L_1$ and $L_2$ are each, independently, represented by a group selected from: an amine which can be the same or different (or joined together to form a bidentate chelating ligand) selected from ammonia, a primary amine, a secondary amine, a non-planar heterocyclic aliphatic amine or a heterocyclic aromatic amine (such as pyridine, imidazole, indazole, bipyridine, phenanthroline and derivatives); a sulphur donor ligand such as dimethyl sulfoxide; a phosphorous donor ligand such as a phosphine; a halogen; an oxygen donor ligand such as water or hydroxyl or hydroxide or methoxy or acetate; and X—Y—Z—.

Where Z is a bidentate O,O' linker and $M^{n+}$ is octahedral $Pt^{4+}$, $Pd^{4+}$, $Ru^{3+}$ or $Ru^{2+}$, $Os^{3+}$ or $Os^{2+}$ then $L_1$-$L_4$ are each, independently, represented by a group selected from: X—Y—Z; an amine which can be the same or different (or joined together to form a bi- or multi-dendate chelating ligand) selected from ammonia, a primary amine, a secondary amine; a non-planar heterocyclic aliphatic amine or a heterocyclic aromatic amine (such as pyridine, imidazole, indazole, bipyridine, terpyridine, phenanthroline and derivatives); a sulphur donor ligand such as dimethyl sulfoxide; a phosphorous donor ligand such as a phosphine; a halogen; and an oxygen donor ligand such as water or hydroxyl or hydroxide or methoxy or acetate.

Where Z is a monodentate O linker and $M^{n+}$ is square planar $Pt^{2+}$ or $Pd^{2+}$ in cis or trans geometry, then $L_3$ and $L_4$ are absent and $L_1$, $L_2$ and $L_5$ are each, independently, represented by a group selected from: an amine which can be the same or different (or joined together to form a bi- or tridendate chelating ligand) selected from ammonia, a primary amine, a secondary amine, a non-planar heterocyclic aliphatic amine or a heterocyclic aromatic amine (such as pyridine, imidazole, indazole, bipyridine, phenanthroline and derivatives); a sulphur donor ligand such as dimethyl sulfoxide; a phosphorous donor ligand such as a phosphine; a halogen; an oxygen donor ligand such as water or hydroxyl or hydroxide or methoxy or acetate; and X—Y—Z.

Where Z is a monodentate ligand and $M^{n+}$ is octahedral $Pt^{4+}$, $Pd^{4+}$, $Ru^{3+}$ or $Ru^{2+}$, $Os^{3+}$ or $Os^{2+}$ then $L_1$-$L_5$ are each, independently, represented by a group selected from: at least one X—Y—Z; an amine which can be the same of different (or joined together to form a bi-, tri- or tetradendate chelating ligand) selected from ammonia, a primary amine, a secondary amine, a non-planar heterocyclic aliphatic amine or a heterocyclic aromatic amine (such as pyridine, imidazole, indazole, bipyridine, terpyridine, phenanthroline and derivatives); a sulphur donor ligand such as dimethyl sulfoxide; a phosphorous donor ligand such as a phosphine; a halogen; and an oxygen donor ligand such as water, hydroxyl, hydroxide, methoxy or acetate.

Thus, in one embodiment, the Metal Complex has a formula selected from the group consisting of:

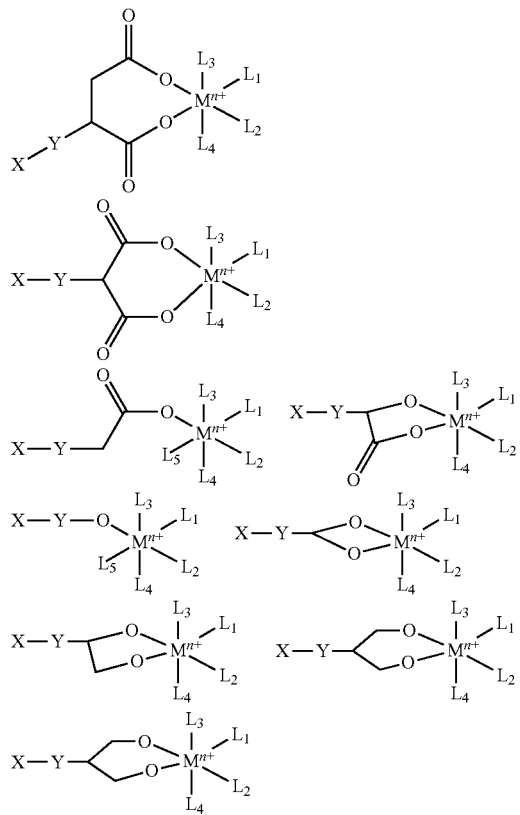

in which X, Y, Z, $M^{n+}$ and $L_1$ to $L_5$ are as defined above.

In a preferred embodiment of the invention, the Metal Complex has a general structure selected from the group consisting of:

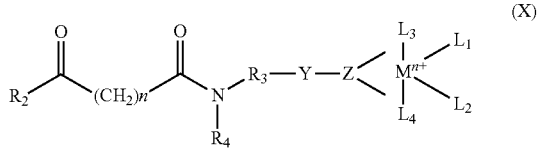

(X)

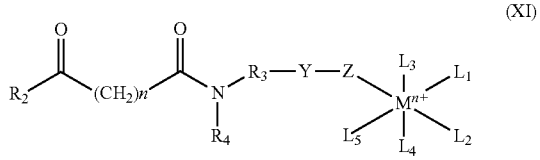

(XI)

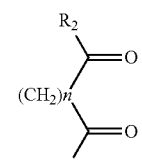

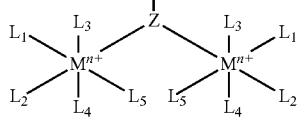

(XII)

in which $R_2$, $R_3$, $R_4$, Y, Z, $M^{n+}$, and $L_1$-$L_5$, are as defined above. In Metal Complex XII above, the ligands $L_1$-$L_5$ on one metal ion may be the same or different to the corresponding ligands $L_1$-$L_5$ on another metal ion. Additionally, the first metal ion may be the same or different to the second or subsequent metal ions.

Typically, $R_2$ is a hydroxyamino, hydroxyl, amino, methylamino, dimethylamino, or a methoxy group. Ideally, $R_2$ is a hydroxylamino group.

Suitably, $R_4$ is a hydrogen atom.

In a preferred embodiment of the invention, $R_3$ is a substituted or unsubstituted phenyl group. Suitably, the phenyl group is substituted with a halogen, for example, a chloro, bromo, fluoro, or iodo group, a methyl, cyano, nitro, trifluoromethyl, amino, methylcyano, or aminocarbonyl group. In another embodiment, $R_3$ is selected from the group consisting of methoxy, cyclohexyl, hydroxyl, benzyloxy, and pyridine.

Thus, the following Metal Complexes are provided:

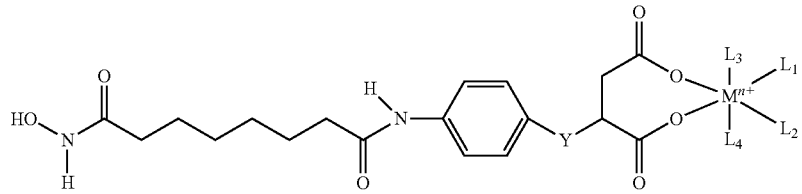

-continued
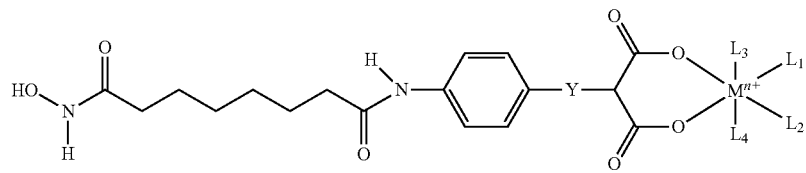
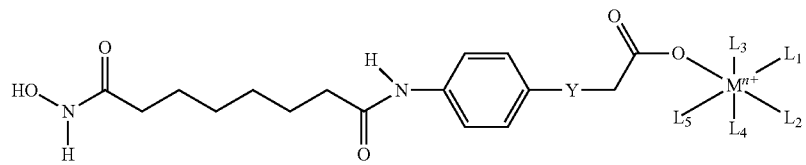
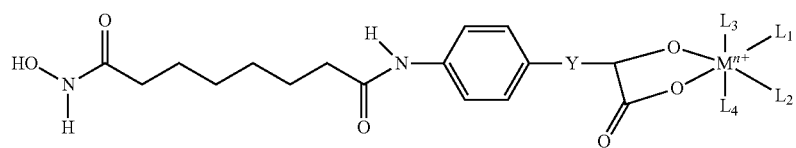
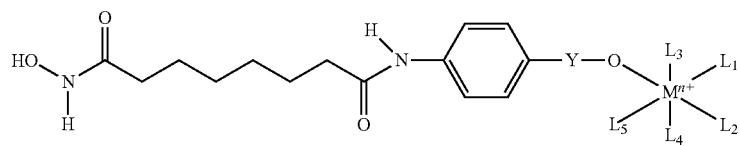
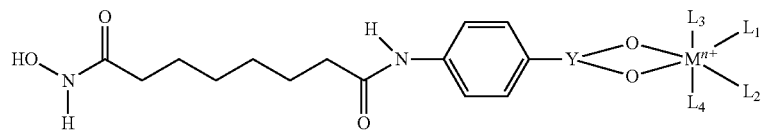
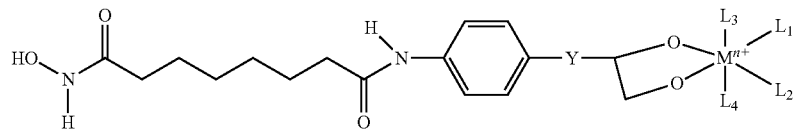
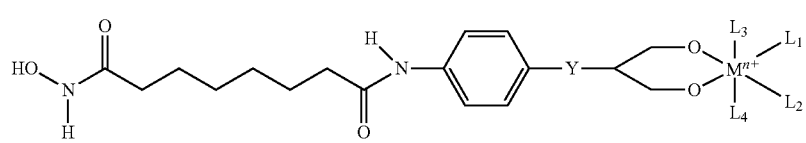
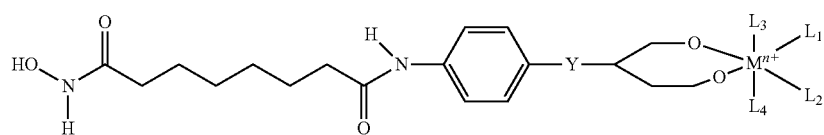

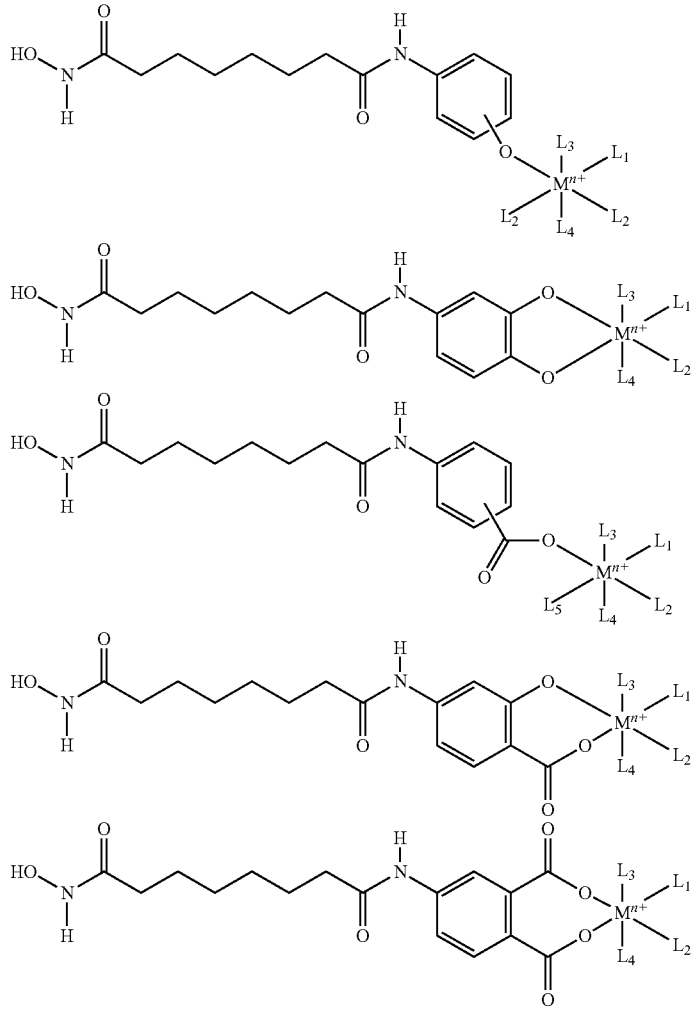
In another embodiment, the Metal Complex has a general formula XIII or XIV or XV:
(XIII)
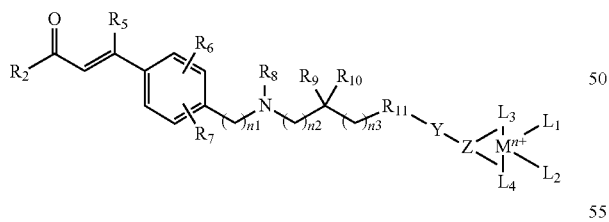
(XIV)
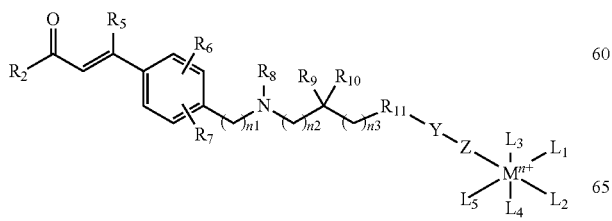

-continued

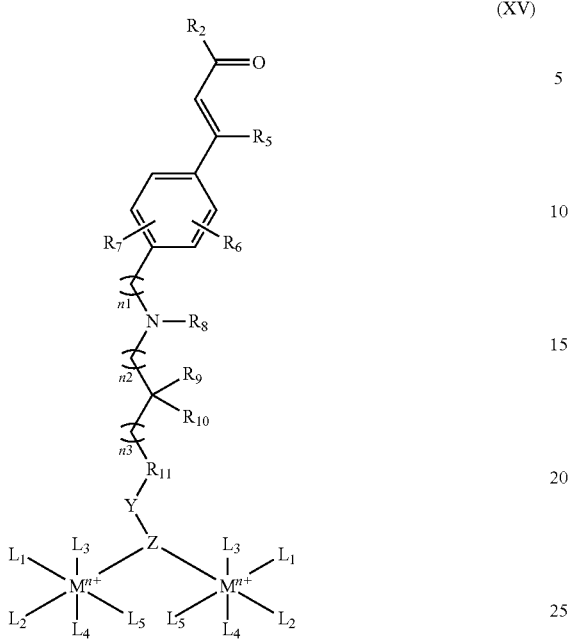

(XV)

in which $R_2$, $R_5$-$R_{11}$, $n_1$-$n_3$, Y, Z, $M^{n+}$, and $L_1$ to $L_5$ are as defined above. In Metal Complex XV above, the ligands $L_1$-$L_5$ on one metal ion may be the same or different to the corresponding ligands $L_1$-$L_5$ on another metal ion. Additionally, the first metal ion may be the same or different to the second or subsequent metal ions.

In another embodiment, the Metal Complex has a general formula XVI, XVII or XVIII:

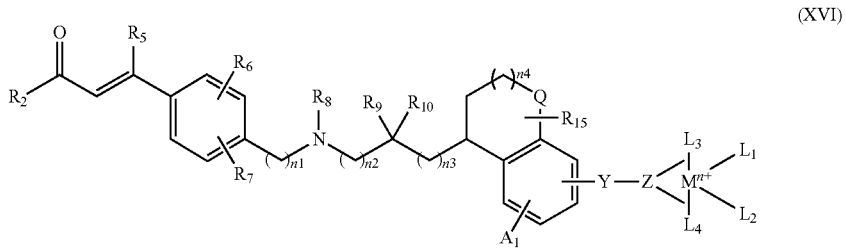

(XVI)

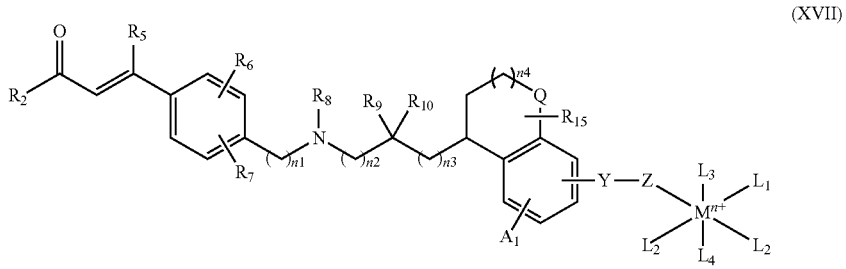

(XVII)

(XVIII)

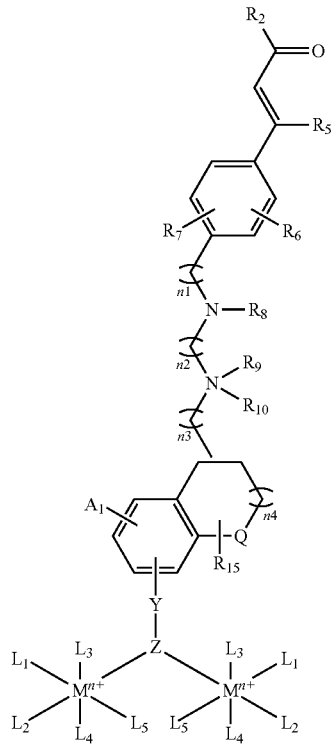

in which $R_2$, $R_5$-$R_{10}$, $R_{15}$, $n_1$-$n_4$, $A_1$, Y, Z, $M^{n+}$, and $L_1$ to $L_5$ are as defined above. In Compound XVIII above, the ligands $L_1$-$L_5$ on one metal ion may be the same or different to the corresponding ligands $L_1$-$L_5$ on another metal ion. Additionally, the first metal ion may be the same or different to the second or subsequent metal ions.

Preferably, the Metal Complex has the structure:

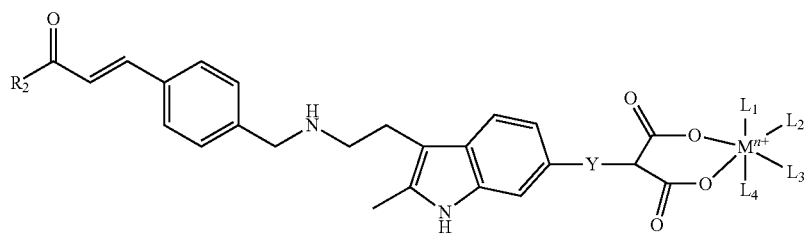

in which $R_2$, Y, $M^{n+}$, and $L_1$ to $L_4$ are as defined above.

In another embodiment, the Metal Complex has a general formula XIX, XX or XXI:

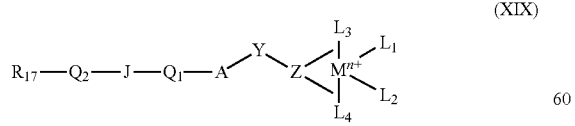

(XIX)

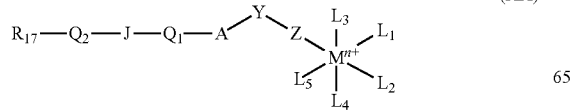

(XX)

-continued

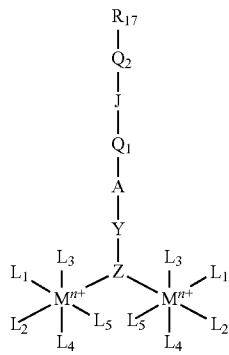
(XXI)

in which $R_{17}$, $Q_1$, $Q_2$, J, A, Y, Z and $M^{n+}$ are as defined above. In Compound XXI above, the ligands $L_1$-$L_5$ on one metal ion may be the same or different to the corresponding ligands $L_1$-$L_5$ on another metal ion. Additionally, the first metal ion may be the same or different to the second or subsequent metal ions.

Preferably, the Metal Complex has the structure:

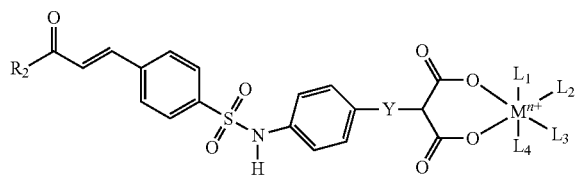

In another aspect, the invention relates to a method of treating a proliferative disorder, for example a cancer, comprising a step of treating an individual with a therapeutically effective amount of a Metal Complex of the invention.

In another aspect, the invention relates to a method of treating a cell to inhibit proliferation of the cell comprising a step of treating the cell with a therapeutically effective amount of an Metal Complex of the invention.

In another aspect, the invention relates to a method of treating a cancer comprising a step of treating an individual with a therapeutically effective amount of a Metal Complex of the invention, wherein the Metal Complex is capable of exhibiting DNA binding and HDAC inhibitory activity in-vivo.

In another aspect, the invention relates to a method of treating a cancer comprising a step of treating an individual with a therapeutically effective amount of a Metal Complex of the invention, wherein the Metal Complex is capable of being hydrolysed in-vivo to provide an active HDAC inhibitor and an active DNA-binding heavy metal ion.

In another aspect, the invention provides a pharmaceutical composition comprising a therapeutically effective amount of a Metal Complex of the invention and a pharmaceutically acceptable carrier.

In another aspect, the invention relates to the use of a Metal Complex of the invention as a medicament.

In another aspect, the invention relates to the use of a Metal Complex of the invention in the manufacture of a medicament for the treatment of cancer.

In another aspect, the invention provides a method of forming a metal complex of the type comprising a HDAC inhibitor coordinated to a DNA-binding heavy metal ion, the method comprising the steps of derivatising the HDAC inhibitor with a mono-dentate, bi-dentate, or chelating, oxygen donor linker group, to provide a monodentate, bidentate, or chelating oxygen donor ligand, and coordinating the DNA-binding heavy metal ion to the monodentate, bidentate, or chelating oxygen donor ligand to provide the metal complex.

Typically, the DNA-binding heavy metal ion is selected from platinum, palladium, ruthenium, osmium, gold, iron, and copper. Preferably, the HDAC inhibitor has a terminal active site inhibiting domain, and a protein surface recognition domain, wherein the protein surface recognition domain is derivatised with the linker. Ideally, the HDAC inhibitor is a hydroxamate-type HDAC inhibitor having a terminal hydroxamate group.

DETAILED DESCRIPTION OF THE INVENTION

Figure 1:
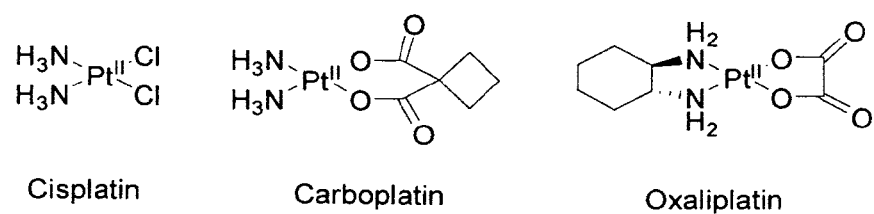
FIG. 1: Chemical structures of Cisplatin, Carboplatin and Oxaliplatin.
Figure 2:
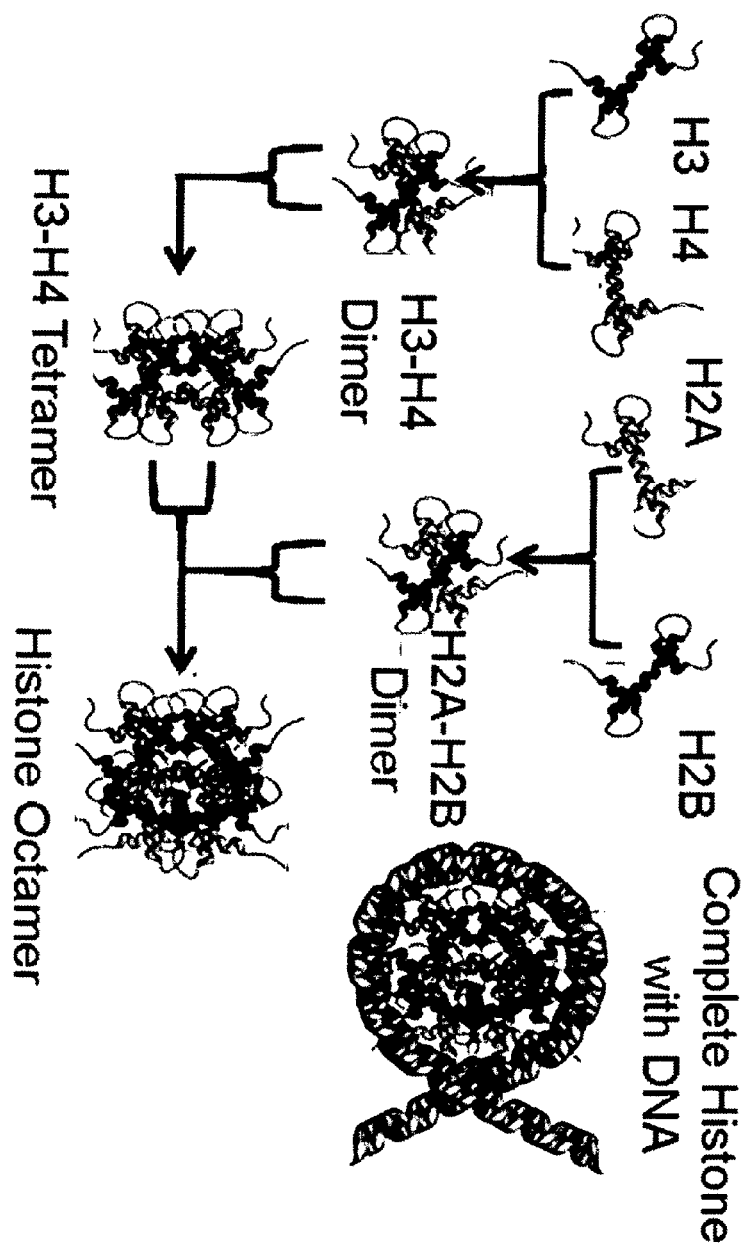
FIG. 2: Representation of the assembly of the core histones into the nucleosome.
Figure 3:
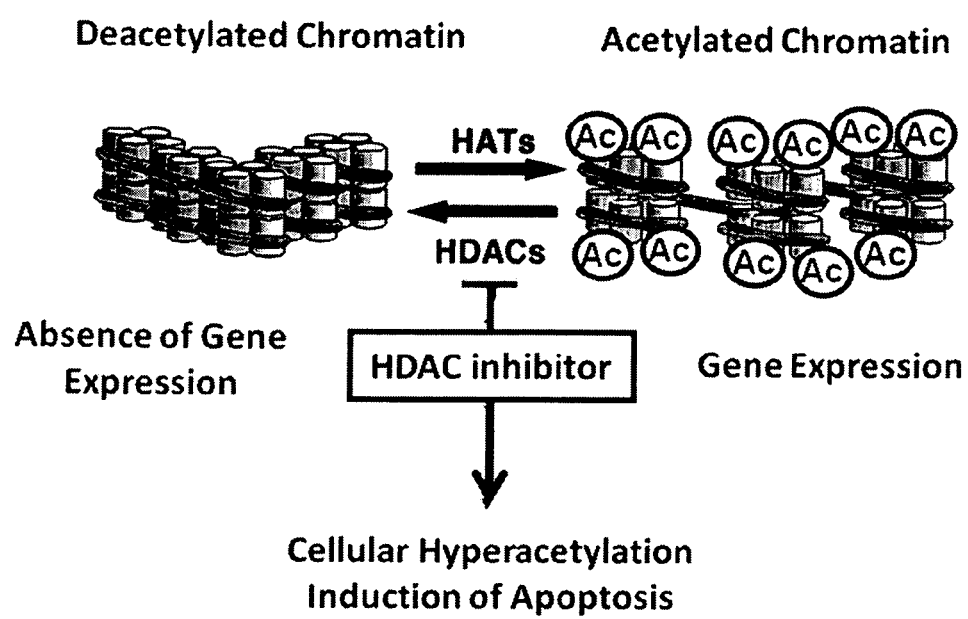
FIG. 3: The histone deacetylase inhibitor (HDACi) causes the activation of gene transcription and induction of apoptosis

In this specification, the term "cancer" should be taken to mean a cancer selected from the group consisting of: fibrosarcoma; myxosarcoma; liposarcoma; chondrosarcom; osteogenic sarcoma; chordoma; angiosarcoma; endotheliosarcoma; lymphangiosarcoma; lymphangioendotheliosarcoma; synovioma; mesothelioma; Ewing's tumor; leiomyosarcoma; rhabdomyosarcoma; colon carcinoma; pancreatic cancer; breast cancer; ovarian cancer; prostate cancer; squamous cell carcinoma; basal cell carcinoma; adenocarcinoma; sweat gland carcinoma; sebaceous gland carcinoma; papillary carcinoma; papillary adenocarcinomas; cystadenocarcinoma; medullary carcinoma; bronchogenic carcinoma; renal cell carcinoma; hepatoma; bile duct carcinoma; choriocarcinoma; seminoma; embryonal carcinoma; Wilms' tumor; cervical cancer; uterine cancer; testicular tumor; lung carcinoma; small cell lung carcinoma; bladder carcinoma; epithelial carcinoma; glioma; astrocytoma; medulloblastoma; craniopharyngioma; ependymoma; pinealoma; hemangioblastoma; acoustic neuroma; oligodendroglioma; meningioma; melanoma; retinoblastoma; and leukemias. In a preferred embodiment, the cancer is selected from the group comprising: breast; cervical; prostate; ovarian, colorectal, lung, lymphoma, and leukemias, and/or their metastases.

"Lower alkyl" means an alkyl group, as defined below, but having from one to ten carbons, more preferable from one to six carbon atoms (eg. "C—C-alkyl") in its backbone structure.

"Alkyl" refers to a group containing from 1 to 8 carbon atoms and may be straight chained or branched. An alkyl group is an optionally substituted straight, branched or cyclic saturated hydrocarbon group. When substituted, alkyl groups may be substituted with up to four substituent groups, at any available point of attachment. When the alkyl group is said to be substituted with an alkyl group, this is used interchangeably with "branched alkyl group". Exemplary unsubstituted such groups include methyl, ethyl, propyl, isopropyl, a-butyl, isobutyl, pentyl, hexyl, isohexyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), Haloalkyl (such as CCl$_3$ or CF$_3$), alkoxy, alkylthio, hydroxyl, carboxy (—COOH), alkyloxycarbonyl (—C(O)R), alkylcarbonyloxy (—OCOR), amino (—NH2), carbamoyl (—NHCOOR— or —OCONHR), urea (—NHCONHR—) or thiol (—SH). Alkyl groups as defined may also comprise one or more carbon double bonds or one or more carbon to carbon triple bonds.

"Lower alkoxy" refers to O-alkyl groups, wherein alkyl is as defined hereinabove. The alkoxy group is bonded to the core compound through the oxygen bridge. The alkoxy group may be straight-chained or branched; although the straight-chain is preferred. Examples include methoxy, ethyloxy, propoxy, butyloxy, t-butyloxy, i-propoxy, and the like. Preferred alkoxy groups contain 1-4 carbon atoms, especially preferred alkoxy groups contain 1-3 carbon atoms. The most preferred alkoxy group is methoxy.

"Halogen" means the non-metal elements of Group 17 of the periodic table, namely bromine, chlorine, fluorine, iodine and astatine.

The terms "alkyl", "cycloalkyl", "heterocycloalkyl", "cycloalkylalkyl", "aryl", "acyl", "aromatic polycycle", "heteroaryl", "arylalkyl", "heteroarylalkyl", "amino acyl", "non-aromatic polycycle", "mixed aryl and non-aryl polycycle", "polyheteroaryl", "non-aromatic polyheterocyclic", "mixed aryl and non-aryl polyheterocycles", "amino", and "sulphonyl" are defined in U.S. Pat. No. 6,552,065, Column 4, line 52 to Column 7, line 39.

The terms "salt" and "counterion" designate a pharmaceutically acceptable salts/counterions and can include acid addition salts such as the hydrochlorides, hydrobromides, phosphates, nitrates, sulphates, hydrogen sulphates, alkylsulphates, arylsulphonates, acetates, benzoates, citrates, maleates, fumarates, succinates, lactates, and tartrates; alkali metal cations such as Na, K, Li; alkali earth metal salts such as Mg or Ca; or organic amine salts. Exemplary organic amine salts are tromethamine (TRIS) salts and amino acid salts (e.g. histidine salts) of the compounds of the invention. Therapeutic Compositions and Methods of Administration The invention provides methods of, and compositions for, treatment and prevention by administration to a subject in need of such treatment of a therapeutically or prophylactically effective amount of an Active Compound of the invention. The subject may be an animal or a human, with or without an established disease.

"Treating" (or "treat") as used herein includes its generally accepted meaning which encompasses prohibiting, preventing, restraining, and slowing, stopping or reversing progression, severity, of a resultant symptom. As such, the methods of this invention encompass both therapeutic and prophylactic administration.

"Effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved;

the degree of or involvement or the severity of the disease; the response of the individual patient; the particular compound administered; the mode of administration; the bioavailability characteristics of the preparation administered; the dose regimen selected; the use of concomitant medication; and other relevant circumstances.

Various delivery systems are known and can be used to administer a compound or composition of the invention, e.g., encapsulation in liposomes, microparticles, microcapsules. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the compounds or compositions of the invention into the circulation system by any suitable route. Pulmonary administration can also be employed, e.g., by use of an inhaler or nebulizer, and formulation with an aerosolizing agent.

It may be desirable to administer the compounds or compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as silastic membranes, or fibers.

Alternatively, the compounds can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327).

In yet another embodiment, the compounds or compositions of the invention can be delivered in a controlled release system. In one embodiment, a pump may be used (see Langer, supra; Sefton, CRC Crit. Ref. Biomed., Eng. 14:201 (1987); Buchwald et al., Surgery 88:75 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The present invention also provides pharmaceutical compositions. Such compositions comprise a therapeutically effective amount of an Active Compound of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals and more particularly in humans.

The term "carrier" refers to a diluent, adjuvant, excipient, or vehicle with which the compound or pro-drug of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol and water.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound or pro-drug of the invention, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline.

In the case of cancer, the amount of the therapeutic of the invention which will be effective in the treatment or prevention of cancer will depend on the type, stage and locus of the cancer, and, in cases where the subject does not have an established cancer, will depend on various other factors including the age, sex, weight, and clinical history of the subject. The amount of therapeutic may be determined by standard clinical techniques. In addition, in vivo and/or in vitro assays may optionally be employed to help predict optimal dosage ranges. The precise dose to be employed in the formulation will also depend on the route of administration, and the seriousness of the cancer, and should be decided according to the judgment of the practitioner and each patient's circumstances. Routes of administration of a therapeutic include, but are not limited to, intramuscularly, subcutaneously or intravenously. Effective doses may be extrapolated from dose-response curves derived from in vitro or animal model test systems.

The invention also provides a pharmaceutical pack or kit comprising one or more containers filled with one or more of the ingredients of the compositions of the invention.

Experimental

Materials and Methods 4-nitrobenzaldehyde, methyl 4-aminobenzoate, methyl 5-aminosalicylate, cinnamic acid, chlorosulphonic acid, dimethyl malonate, piperidine, benzoic acid, malonic acid, $K_2PtCl_4$ and deuterated solvents were all purchased from Aldrich and used without further purification. Suberic anhydride[12] and iodoplatin[13] were synthesized as previously reported. IR spectra were recorded as KBr discs (4000-400 cm$^{-1}$) on a Mattson Genesis II CSI FTIR spectrometer and the spectra analysed using WinFirst software. $^1$H NMR spectra were recorded on a Bruker Avance 400 NMR spectrometer and the spectra analysed using TopSpin 1 software. The residual undeuterated DMSO signal at 2.505 ppm or the $Me_4Si$ signal were used as internal references. UV-VIS spectra were performed on a Helios α Thermo Spectronic Spectrophotometer in a quartz cell. Liquid chromatography-mass spectrometry experiments were performed on a Quattro Micro quadrupole electrospray mass spectrometer (Micromass, Waters Corp., USA): 10 μL of the samples were injected in 300 μL of acetonitrile:water (60:40, v/v). The mass spectrometry data were acquired both in positive and negative ion modes. Elemental analysis (C, H, N) were performed at the Department of Pharmaceutical and Medicinal Chemistry, Royal College of Surgeons in Ireland.

Figure 6:
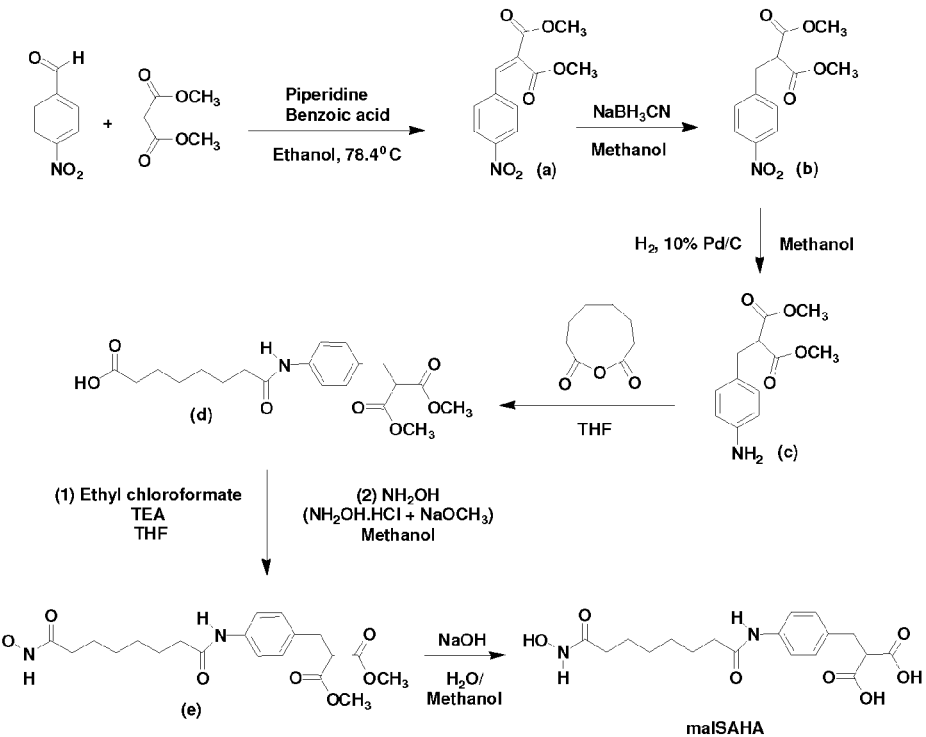
FIG. 6: Synthesis of malSAHA.

Synthesis (1) malSAHA (FIG. 6)

(a) 4-nitrobenzaldehyde (4.90 g, 0.032 mol) and dimethyl malonate (4.46 ml, 0.039 mol) were added to piperidine (0.38 mls, 3.90 mmol) and benzoic acid (0.48 g, 3.90 mmol), which were previously stirred in ethanol (30 ml) for 10 minutes. The reaction was refluxed for five hours, cooled overnight and a yellow crystalline solid (a) collected. Yield: 6.80 g, 80%. $δ_H$ (400 MHz, CDCl$_3$): 8.16 (2H, d, $^3$J 7.0 Hz, aromatic H), 7.73 (1H, s, CH), 7.50 (2H, d, $^3$J 7.0 Hz, aromatic H), 3.81 (3H, s, CH$_3$), 3.78 (3H, s, CH$_3$). $δ_C$ (100 MHz, CDCl$_3$): 166.06, 163.72, 148.50, 139.99, 139.09, 129.91, 129.23, 124.03, 53.09, 53.02.

(b) NaBH$_3$CN (5.97 g, 95.0 mmol) was added to a (6.30 g, 23.8 mmol) in methanol (90 ml) slowly over 15 minutes. The reaction was stirred overnight at room temperature. The pH was adjusted from 10 to 2.5 using dilute HCl. Deionised water (100 ml) was added to the solution and the aqueous layer was extracted with chloroform (3×30 ml). The organic layer was dried with Na$_2$SO$_4$ and the solvent removed in vacuo to give a waxy yellow solid, which subsequently solidified (b). Yield: 6.13 g, 95%. $δ_H$ (400 MHz, CDCl$_3$): 8.08 (2H, d, $^3$J 8.8 Hz, aromatic H), 7.30 (2H, d, $^3$J 8.8 Hz, aromatic H), 3.65 (6H, s, CH$_3$), 3.61 (1H, t, $^3$J 7.8 Hz, CH), 3.25 (2H, d, $^3$J 7.8 Hz, CH$_2$). $δ_C$ (100 MHz, CDCl$_3$): 168.63, 147.03, 145.41, 129.79, 123.84, 52.86, 34.39.

(c) 10% Pd on activated carbon (0.63 g, wet carefully with methanol, 7 ml) was added to b (6.33 g, 23.7 mmol) in methanol (100 ml). The reaction was stirred under an atmosphere of hydrogen overnight at room temperature. The Pd/C was filtered and the solvent from the filtrate was removed in vacuo to give c. Yield: 4.96 g, 88%. $δ_H$ (400 MHz, CDCl$_3$): 6.97 (2H, d, $^3$J 8.4 Hz, aromatic H), 6.60 (2H, d, $^3$J 8.4 Hz, aromatic H), 3.69 (6H, s, CH$_3$), 3.59 (1H, t, $^3$J 8.0 Hz, CH), 3.10 (2H, d, $^3$J 8.0 Hz, CH$_2$). $δ_C$ (100 MHz, CDCl$_3$): 169.39, 145.05, 129.58, 127.58, 115.28, 52.51, 34.06.

(d) To suberic anhydride (3.16 g, 20.2 mmol) dissolved in anhydrous THF (60 ml) and under an atmosphere of argon was added c (4.80 g, 20.2 mmol) dissolved in anhydrous THF (60 ml). The reaction was stirred overnight at room temperature. A white solid, the dianilide, was filtered and dried over P$_2$O$_5$. Deionised water (60 ml) was added to the filtrate, which was subsequently extracted with dichloromethane (3×30 ml). The organic layer was dried with Na$_2$SO$_4$ and the solvent removed in vacuo to give a waxy solid, which was recrystallised from ethyl acetate to give d. Yield: 5.51 g, 67%. $δ_H$ (400 MHz, CDCl$_3$): 7.35 (2H, d, $^3$J 8.4 Hz, aromatic H), 7.15 (1H, s, N—H), 7.06 (2H, d, $^3$J 8.4 Hz, aromatic H), 4.03 (dd, 4H, CH$_2$), 3.64 (6H, s, CH$_3$) 3.55 (1H, t, $^3$J 8.0 Hz, CH), 3.10 (2H, d, $^3$J 8.0 Hz, CH$_2$), 1.62 (2H, p, $^3$J 7.2 Hz, CH$_2$), 1.55 (2H, p, $^3$J 7.2 Hz, CH$_2$), 1.31 (4H, m, CH$_2$). $δ_C$ (100 MHz, CDCl$_3$): 178.02, 171.31, 171.23, 169.20, 129.37, 119.95, 60.43, 53.34, 52.62, 37.54, 34.18, 33.62, 28.72, 28.62, 25.31, 24.44, 21.08, 14.21.

(e) To d (1.93 g, 4.93 mmol) in anhydrous THF (40 ml) and under an atmosphere of argon was added ethyl chloroformate (0.63 ml, 6.55 mmol) and triethylamine (0.99 ml, 7.09 mmol). The mixture was stirred for 30 minutes, to which NH$_2$OH, generated from NH$_2$OH.HCl (0.52 g, 8.18 mmol) and sodium methoxide (1.77 ml, 8.18 mmol) in dry methanol (10 ml), was added. The reaction was stirred for 24 hours. A white solid was filtered and discarded. The solvent from the filtrate was removed in vacuo. Deionised water (30 ml) was added to a waxy solid and extracted with ethyl acetate (3×30 ml). The organic layer was dried with Na$_2$SO$_4$ and the solvent removed in vacuo to give a yellow solid, which was recrystallised from ethyl acetate to give e as a white solid. Yield: 1.2 g, 59%. $δ_H$ (400 MHz, DMSO): 10.34 (1H, s, br, hydroxamic OH), 9.83 (1H, s, br, amide N—H), 8.68 (1H, s, br, hydroxamic N—H), 7.47 (2H, d, $^3$J 8.6 Hz, aromatic H), 7.10 (2H, d, $^3$J 8.6 Hz, aromatic H), 3.80 (1H, t, $^3$J 7.8, CH), 3.60 (3H, s, CH$_3$), 3.01 (2H, d, $^3$J 7.8 Hz, CH$_2$), 2.25 (2H, t, $^3$J 7.2 Hz, CH$_2$), 1.91 (2H, t, $^3$J 7.2 Hz, CH$_2$), 1.52 (2H, p, $^3$J 7.2 Hz, CH$_2$), 1.44 (2H, p, $^3$J 7.2 Hz, CH$_2$), 1.25 (4H, m, CH$_2$). $δ_C$ (100 MHz, CDCl$_3$): 171.07, 169.03, 168.82, 137.86, 131.93, 128.87, 118.98, 52.77, 52.30, 36.29, 33.53, 32.20, 28.37, 25.00.

malSAHA To e (1.14 g, 2.79 mmol) dissolved in methanol (40 ml) was added NaOH (0.88 g, 22.32 mmol) dissolved in deionised water (10 ml). the reaction was stirred at 55° C. for three hours. The pH of the solution was adjusted from 9 to 3 and the reaction mixture was concentrated in vacuo to give a white precipitate, malSAHA. Yield: 0.42 g, 40%. Found C, 56.00; H, 6.31; N, 7.03%. $C_{18}H_{24}N_2O_7$ requires C, 56.83; H, 6.36; N, 7.05%. $v_{max}$/cm$^{-1}$ 3310 br, 3231 br, 3067, 2928, 2858 s, 1712 vs, 1657 vs, 1606 vs. $δ_H$ (400 MHz, d$^6$ DMSO): 12.69 (2H, br, Carboxylic OH), 10.34 (1H, s, br, hydroxamic OH), 9.82 (1H, s, amide N—H), 8.67 (1H, s, br, hydroxamic N—H), 7.46 (2H, d, $^3$J 8.5 Hz, aromatic H), 7.11 (2H, d, $^3$J 8.5 Hz, aromatic H), 3.50 (1H, t, $^3$J 8.0 Hz, CH), 2.95 (2H, d, $^3$J 7.8 Hz, CH$_2$), 2.24 (2H, t, $^3$J 7.25 Hz, CH$_2$), 1.91 (2H, t, $^3$J 7.25 Hz, CH$_2$), 1.52 (2H, p, $^3$J 7.0 Hz, CH$_2$), 1.46 (2H, p, $^3$J 7.0 Hz, CH$_2$), 1.25 (4H, m, CH$_2$). $δ_C$ (100 MHz, DMSO): 171.02, 170.48, 169.05, 137.61, 132.99, 128.89, 118.90, 53.20, 36.28, 33.64, 32.19, 28.37, 25.00. ESI-MS m/z: 381.1 ([M+H]$^+$).

Figure 7:
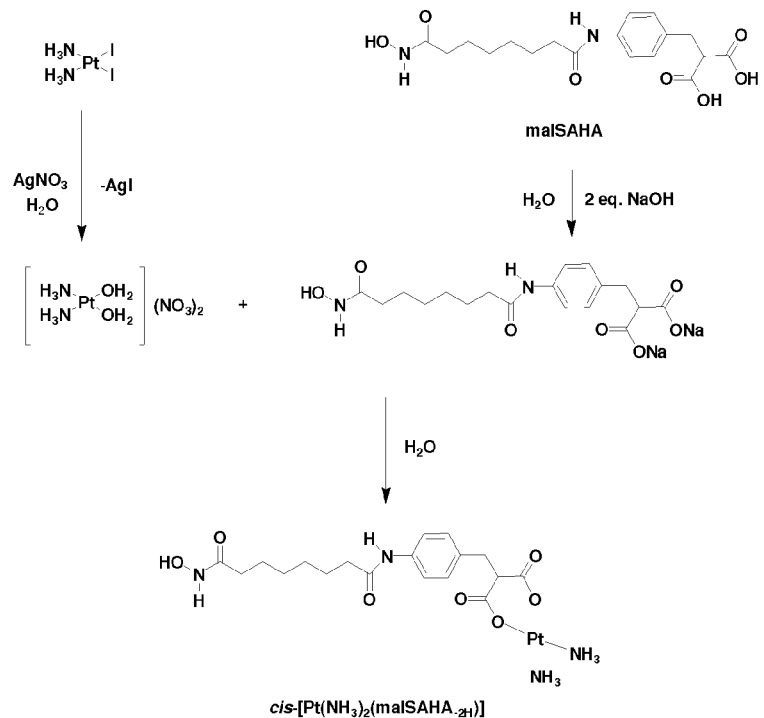
FIG. 7: Synthesis of cis-[Pt$^{II}$(NH$_3$)$_2$(malSAHA$_{-2H}$)].

(2) cis-[Pt(NH$_3$)$_2$(malSAHA$_{-2H}$)].3H$_2$O (FIG. 7)

Iodoplatin (0.3 g, 0.62 mmol) and AgNO$_3$ (0.21 g, 1.21 mmol) in deionised water (15 ml) were stirred overnight in the dark. The insoluble AgI was filtered off and malSAHA (0.26 g, 0.68 mmol) dissolved in an NaOH solution (0.055 g, 1.36 mmol NaOH in 5 ml $H_2O$) was added to the filtrate. The reaction was stirred at room temperature for 3 days. A buff coloured solid was filtered off and dried over $P_2O_5$. Yield: 0.24 g, 66%. Found C, 32.83; H, 4.79; N, 8.89%. $C_{18}H_{34}N_4O_{10}Pt$ requires C, 32.68; H, 5.18; N, 8.47%. $\nu_{max}/cm^{-1}$ 3280 br, 3117 s, 1666 vs, 1654 vs, 1636 vs, 1614, 1530 vs. $\delta_H$ (400 MHz, $d^6$ DMSO): 10.33 (1H, s, br, hydroxamic OH), 9.75 (1H, s, amide N—H), 8.70 (1H, s, br, hydroxamic N—H), 7.39 (2H, d, $^3J$ 8.5 Hz, aromatic H), 7.12 (2H, d, $^3J$ 8.5 Hz, aromatic H), 4.18 (6H, s, br, $NH_3$) 3.95 (1H, t, $^3J$ 6.5 Hz, CH), 2.95 (2H, d, $^3J$ 6.5 Hz, $CH_2$), 2.24 (2H, t, $^3J$ 7.3 Hz, $CH_2$), 1.91 (2H, t, $^3J$ 7.5 Hz, $CH_2$), 1.52 (2H, p, $^3J$ 7.0 Hz, $CH_2$), 1.46 (2H, p, $^3J$ 6.75 Hz, $CH_2$), 1.26 (4H, m, $CH_2$). ESI-MS m/z: 606.2 ([M+H]⁻).

(3) cis-[Pt(NH₃)₂(mal)]

Iodoplatin (0.20 g, 0.41 mmol) and $AgNO_3$ (0.14 g, 0.81 mmol) in deionised water (10 ml) were stirred overnight in the dark. The insoluble AgI was filtered off and malonic acid (0.05 g, 0.46 mmol) was added to the filtrate. The pH of the solution was adjusted from 3.5 to 6.3 using dil. NaOH. The reaction was stirred at room temperature for 24 hours. A grey/white coloured solid was filtered, washed with cold $H_2O$ and dried over $P_2O_5$. Yield: 0.11 g, 58%. Found C, 10.78; H, 2.49; N, 8.13%. $C_3H_8N_2O_4Pt$ requires C, 10.88; H, 2.43; N, 8.46%. $\nu_{max}/cm^{-1}$ 3282, 3266, 3126 s, 1655 vs, 1625 vs, 1582 vs. $\delta_H$ (400 MHz, $d^6$ DMSO): 4.17 (6H, s, br, $NH_3$), 3.20 (2H, s, $CH_2$). ESI-MS m/z: 330.0 ([M+H]⁻).

Figure 8:
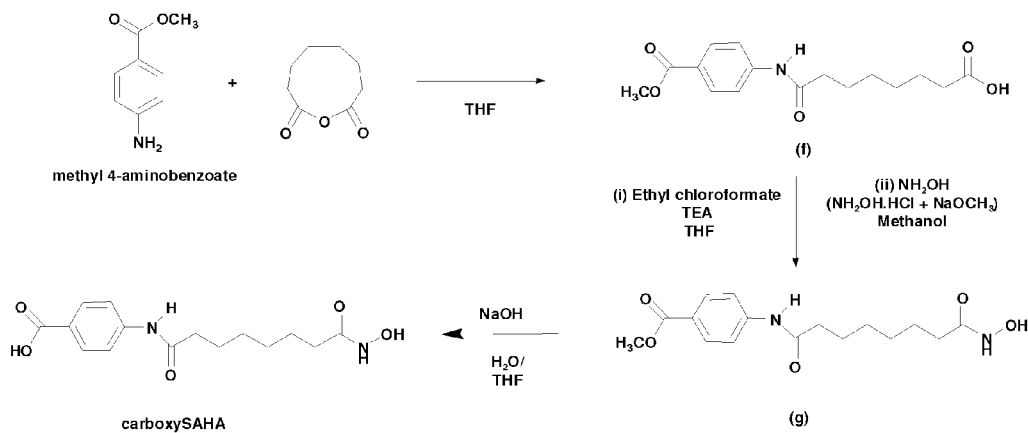
FIG. 8: Synthesis of carboxySAHA.

(4) carboxySAHA (FIG. 8)

(f) To suberic anhydride (4.0 g, 25.6 mmol) and methyl 4-aminobenzoate (3.87 g, 25.6 mmol) under an atmosphere of argon was added anhydrous THF (80 ml). The reaction was stirred overnight at room temperature. A white solid, was filtered and discarded. Deionised water (60 ml) was added to the filtrate, which was subsequently extracted with chloroform (3×30 ml). The organic layer was dried with $Na_2SO_4$ and the solvent removed in vacuo to give f. Yield: 6.8 g, 86%. $\delta_H$ (400 MHz, DMSO): 12.03 (1H, br, s, carboxylic OH), 10.26 (1H, br, s, OH), 9.87 (1H, br, s NH amide), 7.89 (2H, d, $^3J$ 7.0 Hz, aromatic H), 7.07 (2H, d, $^3J$ 8.7 Hz, aromatic H), 3.81 (3H, s, $CH_3$) 2.31 (2H, d, $^3J$ 7.5 Hz, $CH_2$), 2.17 (2H, d, $^3J$ 7.3 Hz, $CH_2$), 1.56 (2H, p, $^3J$ 7.3 Hz, $CH_2$), 1.46 (2H, p, $^3J$ 7.2 Hz, $CH_2$), 1.26 (4H, m, $CH_2$).

(g) To f (4.15 g, 13.5 mmol) in anhydrous THF (60 ml) and under an atmosphere of argon was added ethyl chloroformate (1.72 ml, 18.00 mmol) and triethylamine (2.72 ml, 19.44 mmol). The mixture was stirred for 30 minutes, to which $NH_2OH$, generated from $NH_2OH.HCl$ (1.56 g, 22.4 mmol) and sodium methoxide (4.84 ml, 22.4 mmol) in dry methanol (15 ml), was added. The reaction was stirred for 24 hours. A white solid was filtered and discarded. Deionised water (30 ml) was added to the filtrate and extracted with ethyl acetate (3×30 ml). The organic layer was dried with $Na_2SO_4$ and the solvent removed in vacuo to give g. Yield: 2.71 g, 62%. $\delta_H$ (400 MHz, DMSO): 10.38 (1H, s, br, hydroxamic OH), 10.26 (1H, s, br, amide NH), 8.72 (1H, s, br, hydroxamic N—H), 7.89 (2H, d, $^3J$ 8.7 Hz, aromatic H), 7.71 (2H, d, $^3J$ 8.7 Hz, aromatic H), 3.81 (3H, s, $CH_3$), 2.31 (2H, t, $^3J$ 7.4 Hz, $CH_2$), 1.91 (2H, t, $^3J$ 7.2 Hz, $CH_2$), 1.54 (2H, p, $^3J$ 7.1 Hz, $CH_2$), 1.45 (2H, p, $^3J$ 6.7 Hz, $CH_2$), 1.26 (4H, m, $CH_2$).

carboxySAHA To g (0.96 g, 3.12 mmol) dissolved in THF (20 ml) was added NaOH (0.87 g, 21.86 mmol) dissolved in deionised water (5 ml). The reaction was refluxed for 45 minutes. The pH of the solution was adjusted to 3 and the reaction mixture was concentrated in vacuo to give a white precipitate, carboxySAHA. Yield: 0.56 g, 58%. Found C, 52.24; H, 6.68; N, 7.85%. $C_{15}H_{24}N_2O_7$ requires C, 52.32; H, 7.02; N, 8.13%. $\delta_H$ (400 MHz, $d^6$ DMSO): 12.59 (1H, br, carboxylic OH), 10.37 (1H, s, br, hydroxamic OH), 10.26 (1H, s, amide N—H), 8.69 (1H, s, br, hydroxamic N—H), 7.86 (2H, d, $^3J$ 8.6 Hz, aromatic H), 7.70 (2H, d, $^3J$ 8.6 Hz, aromatic H), 2.32 (2H, t, $^3J$ 8.4 Hz, $CH_2$), 1.92 (2H, t, $^3J$ 7.6 Hz, $CH_2$), 1.55 (2H, p, $^3J$ 7.2 Hz, $CH_2$), 1.46 (2H, p, $^3J$ 7.2 Hz, $CH_2$), 1.26 (4H, m, $CH_2$). ESI-MS m/z: 307.56 ([M+H]⁻).

Figure 9:
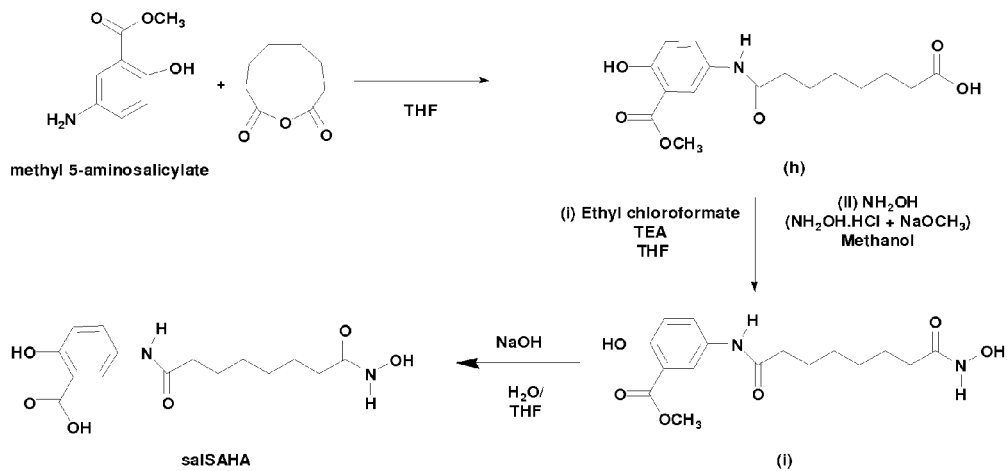
FIG. 9: Synthesis of salSAHA.

(5) salSAHA (FIG. 9)

(h) To suberic anhydride (2.24 g, 14.4 mmol) and methyl 5-aminosalicylate (2.4 g, 14.4 mmol) under an atmosphere of argon was added anhydrous THF (60 ml). The reaction was stirred overnight at room temperature. A white solid, was filtered and discarded. Deionised water (60 ml) was added to the filtrate, which was subsequently extracted with dichloromethane (3×30 ml). The organic layer was dried with $Na_2SO_4$ and the solvent removed in vacuo to give h. Yield: 3.05 g, 65%. $\delta_H$ (400 MHz, DMSO): 12.00 (1H, br, s, carboxylic OH), 10.26 (1H, br, s, OH), 9.87 (1H, br, s, amide NH), 8.11 (1H, dd, $^4J$ 2.6 & $^3J$ 16.0 Hz, aromatic H), 7.62 (1H, dd, $^4J$ 2.6 & $^3J$ 9.0 Hz, aromatic H), 6.92 (1H, dd, $^4J$ 1.4 & $^3J$ 9.0 Hz, aromatic H), 3.89 (3H, s, $CH_3$) 2.21 (1H, t, $^3J$ 7.4 Hz, $CH_2$), 2.17 (3H, m, $CH_2$), 1.53 (2H, p, $^3J$ 7.0 Hz, $CH_2$), 1.44 (2H, p, $^3J$ 7.0 Hz, $CH_2$), 1.24 (4H, m, $CH_2$).

(i) To h (1.20 g, 3.70 mmol) in anhydrous THF (45 ml) and under an atmosphere of argon was added ethyl chloroformate (0.47 ml, 4.94 mmol) and triethylamine (0.75 ml, 5.30 mmol). The mixture was stirred for 30 minutes, to which $NH_2OH$, generated from $NH_2OH.HCl$ (0.43 g, 6.20 mmol) and sodium methoxide (1.33 ml, 6.20 mmol) in dry methanol (7 ml), was added. The reaction was stirred for 24 hours. A white solid was filtered and discarded. Deionised water (30 ml) was added to the filtrate and extracted with ethyl acetate (3×30 ml). The organic layer was dried with $Na_2SO_4$ and the solvent removed in vacuo to give i. Yield: 0.96 g, 77%. $\delta_H$ (400 MHz, DMSO): 10.31 (1H, s, br, OH), 10.25 (1H, br, s, OH), 9.86 (1H, s, N—H), 8.68 (1H, s N—H), 8.14 (1H, s, aromatic H), 7.62 (1H, d, $^3J$ 7.8 Hz, aromatic H), 6.92 (1H, d, $^3J$ 8.6 Hz, aromatic H), 3.89 (3H, s, $CH_3$), 2.25 (2H, d, $^3J$ 7.8 Hz, $CH_2$), 1.91 (2H, t, $^3J$ 7.2 Hz, $CH_2$), 1.48 (4H, p, $CH_2$), 1.25 (4H, m, $CH_2$).

salSAHA To i (0.80 g, 2.36 mmol) dissolved in THF (20 ml) was added NaOH (0.56 g, 14.19 mmol) dissolved in deionised water (5 ml). The reaction was refluxed for 45 minutes. The pH of the solution was adjusted to 3 and the reaction mixture was concentrated in vacuo to give a light brown precipitate, salSAHA. Yield: 0.34 g, 42%. Found C, 55.42; H, 6.58; N, 8.86%. $C_{15}H_{20}N_2O_6$ requires C, 55.55; H, 6.22; N, 8.64%. $\delta_H$ (400 MHz, $d^6$ DMSO): 11.32 (1H, br, s, OH), 10.43 (1H, s, OH), 9.83 (1H, s, NH), 9.31 (1H, br, s, OH), 8.75 (1H, s, NH), 7.91 (1H, d, $^4J$ 2.8 Hz), 7.53 (1H, dd, $^3J$ 2.8 Hz and $^3J$ 8.8 Hz), 6.90 (1H, d, $^3J$ 8.8 Hz), 2.24 (3H, m, $CH_2$), 1.98 (1H, t, $^3J$ 7.2 Hz, $CH_2$), 1.51 (4H, 2×p, $CH_2$), 1.31 (4H, m, $CH_2$). ESI-MS m/z: 323.52 ([M+H]⁻).

Figure 10:
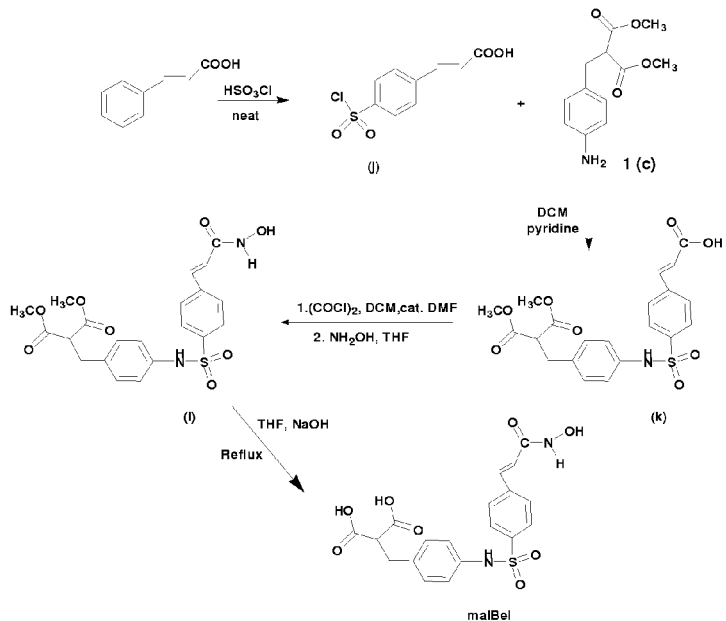
FIG. 10: Synthesis of malBel.

(6) malBel (FIG. 10)

(j) Cinnamic acid 1 (7.90 g, 0.054 mmol) was added slowly to neat chlorosulphonic acid (28.60 ml, 430 mmol). The mixture was stirred at 0° C. for 3 hours and then at room temperature for three days. The dark viscous syrup was poured onto ice affording a white precipitate which was filtered, washed with water and recrystallised from dioxane to give j. Yield: 2.73 g, 34%. Found C, 44.10; H, 3.01%. $C_9H_7ClO_4S$ requires C, 43.82; H, 2.86%. $\delta_H$ (400 MHz, $d^6$ DMSO): 13.80 (1H s), 7.62 (2H, d, J 8.5 Hz), 7.60 (2H, d, J 8.5), 7.54 (1H, d, J 16.0 Hz), 6.53 (1H, d, J 16.0 Hz).

(k) j (2.25 g, 9.15 mmol) was added to a solution of 1 (c) (5.0 g, 18.30 mmol) and pyridine (3 ml) in dry DCM (30 ml). The resultant solution was stirred at 40° C. for 1 hr. The mixture was evaporated and the residue partitioned between ethyl acetate and 6M HCl. The organic layer was collected, washed with water and brine, dried ($Na_2SO_4$), and evaporated to afford a pinkish white-solid (k): Yield: 3.18 g, 35%. Found C, 56.34; H, 4.80; N, 3.08%. $C_{21}H_{21}NO_8S$ requires C, 56.37; H, 4.73; N, 3.13%. $\delta_H$ (400 MHz, $d^6$ DMSO): 12.70 (1H, s), 10.36 (1H, s), 7.90 (2H, d, J 8.5 Hz), 7.75 (2H, d, J 8.5 Hz), 7.65 (1H, d, J 16.0 Hz), 7.10 (2H, d, J 8.5 Hz), 7.00 (2H, d, J 8.5 Hz), 6.65 (1H, d, J 16.0 Hz), 3.85 (1H, t, J 8.50 Hz), 3.61 (6H, s), 3.02 (2H, d, J 16.0 Hz).

(l) To a suspension of (k) (2.30 g, 5.14 mmol) in 25 ml dry DCM, was added oxalyl chloride (1.54 ml, 16.70 mmol) and one drop of catalytic DMF. The resultant solution was refluxed for 1 hr. The solvent was evaporated and the residue was dried in vacuo and redissolved in 30 ml dry THF, to which $NH_2OH$, generated from reaction of hydroxylamine hydrochloride (1.78 g, 25.70 mmol) in THF (25 ml) and a saturated $NaHCO_3$ solution. (20 ml) was added. The resultant solution was stirred at room temperature for 1 hour. The mixture was partitioned between ethyl acetate and 2M HCl. The organic layer was washed successively with water and brine, evaporated and the residue recrystallised from ethyl acetate to give 1. Yield: 1.47 g, 62%. Found C, 52.54; H, 4.89; N, 5.88%. $C_{21}H_{22}N_2O_8S.H_2O$ requires C, 52.49; H, 5.03; N, 5.83%. $\delta_H$ (400 MHz, $d^6$ DMSO): 10.88 (1H, s), 10.27 (1H, s), 9.15 (1H, s), 7.70 (4H, q, J 8.5 Hz), 7.50 (1H, d, J 16.0 Hz), 7.01 (2H, d, J 8.5 Hz), 6.98 (2H, d, J, 8.5 Hz), 6.53 (1H, d, J 16.0 Hz), 3.78 (1H, t, J 8.50), 3.55 (6H, s,), 2.96 (2H d, J 16.0 Hz).

malBel To a suspension of l (1.44 g, 3.00 mmol) in 30 ml THF, was added NaOH (0.88 g, 22.32 mmol) dissolved in deionised water 10 ml and the resultant solution was stirred at 75° C. for 1 hr. The mixture was partitioned between ethyl acetate and 2M HCl. The organic layer was washed successively with water and brine, evaporated and the residue recrystallized from ethyl acetate to give malBel. Yield: 1.00 g, 74%. Found C, 51.11; H, 4.52; N, 5.51%. $C_{19}H_{22}N_2O_9S$ requires C, 51.35; H, 4.80; N, 5.84%. $\delta_H$ (400 MHz, $d^6$ DMSO): 12.77 (1H, s), 10.95 (1H, s), 10.32 (1H, s), 9.22 (1H, s), 7.78 (4H, q, J 8.5 Hz), 7.53 (1H, d, J 16.0 Hz), 7.01 (2H, d, J 8.5 Hz), 7.00 (2H, d, J, 16.0 Hz), 6.60 (1H, d, J 16.0 Hz), 3.55 (1H, t, J 8.50), 2.96 (2H d, J 16.0 Hz). ESI-MS m/z: 435.1 ([M+H]$^+$).

Figure 11:
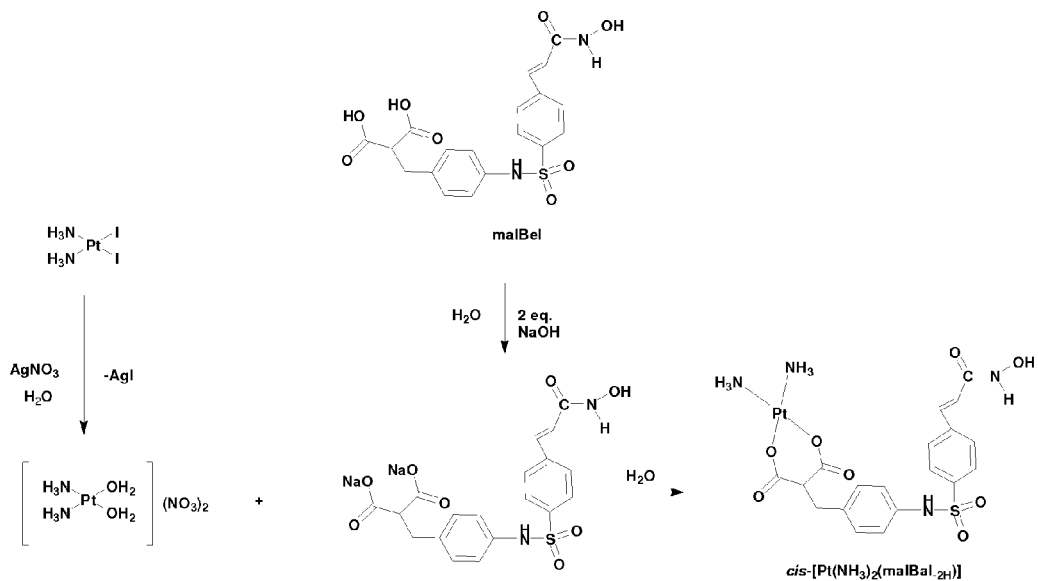
FIG. 11: Synthesis of cis-[Pt$^{II}$(NH$_3$)$_2$(malBel$_{-2H}$)].

(7) cis-[Pt(NH$_3$)$_2$(malBel$_{-2H}$)].1.5H$_2$O (FIG. 11)

Iodoplatin (0.30 g, 0.62 mmol) and AgNO$_3$ (0.21 g, 1.21 mmol) in deionised water (15 ml) were stirred for three hours at 55° C. The insoluble AgI was filtered off. To the filtrate, malBel (0.307 g, 0.68 mmol) dissolved in NaOH (0.055 g, 1.36 mmol) in 5 ml water was added and stirred at room temperature for 3 days. The light yellow precipitate was filtered, washed with ethanol and diethylether and dried over P$_2$O$_5$, to afford cis-[Pt(NH$_3$)$_2$(malBel$_{-2H}$)]. Yield: 0.25 g, 82%. Found C, 31.83; H, 3.52; N, 7.88%. $C_{19}H_{22}N_4O_8PtS.1.5H_2O$ requires C, 32.07; H, 3.54; N, 7.87%. $\delta_H$ (400 MHz, $d^6$ DMSO): 9.22 (1H, s), 7.78 (4H, q, J 8.5 Hz), 7.53 (1H, d, J 16.0 Hz), 7.01 (2H, d, J 8.5 Hz), 7.00 (2H, d, J, 16.0 Hz), 6.60 (1H, d, J 16.0 Hz), 4.25 (s, 6H), 3.86 (1H, t, J 8.50), 2.97 (2H d, J 16.0 Hz). ESI-MS m/z: 660.1 ([M+H]$^-$).

Cell Cultures

Cells were cultured in the appropriate media. A2780 P and A2780 cisR human ovarian carcinoma cells for example were cultured in RPMI 1640 supplemented with 10% Foetal Bovine Serum (Biosera, East Sussex, UK), 2 mM Glutamine (EuroClone, Wheterby, UK) and 100 U/mL penicillin and 100 μg/mL streptomycin (EuroClone, Wheterby, UK). In order to retain resistance 1 μM cisplatin was added to the media of the A2780 cisR cells every third passage. A2780 cisR cells are resistant to cisplatin through a combination of decreased uptake, enhanced DNA repair/tolerance, and elevated reduced glutathione levels In addition Normal Neonatal Human Dermal Fibroblast, NHDF, cells were cultured in Fibroblast Basal Medium (FBM®, Clonetics, Walkersville, USA) supplemented with hFGF-B, insulin, 5% FBS and gentamicin/amphotericin-B (FGM®-2 SingleQuots, Clonetics, Walkersville, USA).

All cells were kept in a humidified atmosphere with 5% CO$_2$ at 37° C.; cells from confluent monolayers were removed from flasks by trypsin/EDTA solution and their viability determined by the trypan blue exclusion test.

In Vitro Cytotoxicity Evaluation

Cell growth was determined by the [3-(4,5-dimethylthiazol-2-yl)-5-(3-carboxymethoxyphenyl)-2-(4-sulfophenyl)-2H-tetrazolium, inner salt, (MTS test, Promega, Southampton, UK), a colorimetric assay based on the ability of the viable cells to reduce a soluble yellow tetrazolium salt to blue formazan. 10,000 ovarian cancer cells or 3,000 fibroblast cells for example were seeded per well onto 96-well plates in 100 μl of the appropriate culture medium. 24 hr after sowing the cells, the media was removed and the cells were treated by adding 100 μl of the compound media solutions at the appropriate concentrations. cis-[Pt(NH$_3$)$_2$(malSAHA$_{-2H}$)], cisplatin and cis-[Pt(NH$_3$)$_2$(mal)] were prepared freshly in cell culture media. SAHA was freshly prepared in dimethylsulfoxide (dmso) and diluted in culture media prior to MTS assay. The maximum percentage of dmso present in any well was less than 0.1% (v/v). cis-[Pt(NH$_3$)$_2$(malBel$_{-2H}$)], belinostat and malbelinostat were freshly prepared in dimethyl formamide (DMF) and diluted in culture media prior to the MTS assay. The maximum percentage of DMF present in any well was 0.5% (v/v). A range of concentrations between 1 μM and 100 μM was used.

After 72 hr of treatment, 20 μl of the MTS reagent was added to each well and the plates incubated for 2 hr at 37° C. The absorbance was measured at 490 nm[14, 15] using a Wallac 1420 Victor 3V plate reader (Perkin-Elmer Life Sciences, Boston, USA). The percentages of surviving cells relative to untreated controls were determined. The IC$_{50}$ values defined as the drug concentration which inhibits cell growth by 50% were estimated graphically from dose-response plots.

Histone Deacetylase Inhibitory Activity

The ability of the test compounds to inhibit HDAC1 was investigated in triplicate using Cayman's HDAC1 Inhibitor Screening Assay Kit (Cayman Chemicals, Ann Arbor, USA) and Trichostatin A as a control, according to the manufacturer's instructions. The assay provides a fast two-step fluorescence-based method for measuring HDAC activity. Briefly, in the first step an acetylated lysine residue was incubated with HDAC1 and potential inhibitors. Deacetylation sensitises the substrate so that treatment with the HDAC developer in the second step releases a fluorescent product. The fluorescent reaction product was analysed using a plate reader with an excitation wavelengths of 350 nm and emission wavelengths of 460 nm. Stock solutions of investigated $Pt^{II}$ complexes and Trichostatin A, SAHA and malSAHA were prepared freshly in buffer and dmso respectively and diluted to various working concentrations. The $IC_{50}$ values defined as the drug concentration which inhibits HDAC1 activity by 50%, were determined by graphing percentage of initial activity (control, no inhibitor) as a function of inhibitor concentration.[16]

DNA Unwinding Experiment

Platinum compounds, such as cisplatin, that unwind the DNA duplex reduces the number of supercoils in closed circular DNA so that their number decreases. This decrease upon binding of unwinding agents causes a decrease in the rate of migration of DNA through agarose gel. Unwinding of closed circular supercoiled pUC19 plasmid DNA incubated with cis-$[Pt^{II}(NH_3)_2(malSAHA_{-2H})]$ was assayed by an agarose gel mobility shift assay. Samples of plasmid DNA were incubated with platinum complexes at 37° C. in the dark for 48 h. All samples were subjected to electrophoresis on 1% native agarose gel running at 25° C. with TAE buffer and the voltage set at 25 V. The gels were then stained with EtBr, followed by photography with transilluminator.[16]

Determination of Pt Binding to DNA in Cultured Cells

Pt DNA binding of Pt complexes was measured in SW480 cells (colon cancer) and CH1 cells (lymphoma) or alternatively A2780 P and A2780 cisR cells (sensitive and resistant to cisplatin respectively). The cells were seeded in 60 mm tissue culture dishes with 10 ml of their respective medium. After overnight incubation the medium was removed and replaced with 10 ml of the respective medium containing a platinum complex giving a final concentration of 43 or 40 µM depending on the experiment. The cells were incubated with a given Pt complex for either 2 or 4 h depending on the experiment. The cells were trypsinised and centrifuged. The supernatant was removed and the cells washed twice with 1×PBS and centrifuged. The pellet was re-suspended in DNA buffer to which Proteinase K (20 mg/mL) and 10% SDS were added. After a gentle shake and incubation at 45° C. for two hours, RNAse (100 mg/mL) was added and the cells were incubated at 37° C. overnight. The volume of supernatant was noted and an equal volume of phenol was added.

The resulting mixture was shook for 10 min, then centrifuged for 10 min at 10° C. The supernatant was transferred into a new centrifuge tube (15 ml) and the volume was noted. To this was added an equal volume of phenol and chloroform/isoamylalcohol (24:1). The resulting mixture was shook for 10 min, then centrifuged for 10 min at 10° C. (3000 RPM). The supernatant was transferred into a new centrifuge tube (15 mL) and the volume was noted. To this was added an equal volume of chloroform. The resulting mixture was shook for 10 min, then centrifuged for 10 min at 10° C. The supernatant was transferred into a new centrifuge tube (15 mL) and the volume was noted. To this was added a volume that is 1/10 of the supernatant of 3 M sodium acetate (Ph 5.2) and three times the volume of cold 100% isopropanol (from freezer). The solution was shook gently until the DNA is precipitated. The DNA was transferred to a tube with 70% ethanol (30 mL) using a sterile glass pipette. The resulting mixture was placed on an inverting rack for 2 h to thoroughly rinse. The DNA was then transferred into a sterile eppendorf and centrifuged for 20 min. The resulting pellet was dried in a SpeedVac for 5 min. The DNA was dissolved in 300-500 µL of sterile water and placed in an eppendorf thermomixer shaker overnight at 37° C. (or until the DNA dissolved). The absorbance of the DNA by was measured by UV spectrophotometry at 260 nm and 280 nm and the concentration of DNA calculated. Platinum bound to DNA was determined by ICP-MS.

Cellular Uptake of Pt

Cellular uptake of Pt compounds was measured in SKBR, SW480, A549, A2780P and CH1 cells. The cells were seeded in 60 mm tissue culture dishes with 10 mL of their respective medium and after overnight incubation, the cells were treated with the Pt complexes for 72 h at 10 µM concentration. The cell monolayers at the end of the incubation with the Pt complexes were washed (twice) with ice-cold phosphate buffered saline (PBS), trypsinized and harvested into cold (4° C.) PBS. Cell suspensions were centrifuged and the pellets were stored in PBS at −80° C. until assayed. Afterward, the pellets were digested by high pressure microwave mineralization and Pt content was determined by flameless atomic absorption spectrophotometry (FAAS). The results of cellular Pt uptake were corrected for adsorption effects. All experiments were made in triplicate.[17]

Inhibition of DNA Synthesis

DNA synthesis was determined using 5-bromo-2-deoxyuridine (BrdU) colourimetric incorporation assay.[18] A2780 P and A2780 cisR cells were seeded into 96 well plates and allowed to adhere overnight. All test agents were added and incubated for 72 hr prior to the addition of BrdU (10 µM per well). Plates were then incubated at 37° C. for 4 h and incorporation was quantified by ELISA (Calbiochem).

Morphological Analysis

Preparations of A2780 P and A2780-cisR cells were exposed to test agents for 72 hr and stained with methylene blue and eosin[19]. Drug-treated cells were grown in petri dishes, washed once with PBS, once with PBS:methanol (1:1, v/v), and then fixed in 100% (v/v) methanol for 10 min. Following fixation, cell monolayers were rinsed with anhydrous methanol and stained with methylene blue and eosin for 2 min. Monolayers were then agitated for a further 2 min, destained by rinsing under a gentle stream of water and then finally rinsed with distilled water. Phase contrast microscopy was carried out using a Ceti-phase contrast microscope.

Drug-treated cells were also stained using a DNA-binding agent commonly used to stain nuclei and visualise nuclear morphology and DNA condensation, namely 4,6-diamidino-2-phenylindole (DAPI). Briefly, a monolayer of drug-treated cells was washed in PBS and fixed with 4% (w/v) paraformaldehyde for 30 min at room temperature. These cells were then permeabilized with 0.2% (v/v) Triton X in PBS and incubated with 1 µg/ml of DAPI for 30 min. Cells were again washed three times with PBS and viewed using a fluorescent microscope with 340/380 nm excitation filter at 250× magnification. Apoptotic cells were confirmed by identification of intensely stained, fragmented nuclei and condensed chromatin.

Caspase Assays to Detect Cell Death

Activation of ICE-family proteases/caspases initiates apoptosis in mammalian cells.[20] A2780 P and A2780 cisR cells were incubated with test agents at concentrations equivalent to the $IC_{50}$ and $IC_{75}$ for 72 hr. Both floating and attached cells were collected by centrifugation. Cells, at a density of 1.5×$10^6$ cells/ml were washed with PBS and then re-suspended in chilled cell lysis buffer (supplied in the Caspase-3 colourimetric assay kit, Calbiochem, UK). Cells were incubated on ice for 10 min and then centrifuged for 1 min at 10,000 g. The cytosolic fraction (supernatant) was collected into a fresh tube and 50 µl (2 mg/ml) of each protein sample was transferred to a 96 well plate and diluted with lysis buffer. A 50 µl aliquot of X2 reaction buffer, containing 10 mM DTT was added, followed by 5 µl of 4 mM DEVD-pNA substrate to give a final concentration of 200 µM. The plate was then incubated at 37° C. for 1-2 h. OD was determined at 400 nm using an Anthos HT-II microtitreplate reader. The fold increase in caspase-3 and -9 activities was determined by comparing results to that obtained with un-induced control.

Effects of Pt Complexes on Cell Cycle Progression

A2780 P and A2780 cisR cells were grown in T75 flasks to 70% confluency and exposed to test agents at concentrations equivalent to the $IC_{50}$ and $IC_{75}$ for 72 hr. Both floating and attached cells were collected by centrifugation, washed twice in ice-cold PBS, pH 7.4, harvested by scraping with a rubber policeman, and then collected by centrifugation. The effect of drug treatment on cell cycle progression was determined using flow cytometric analysis according to the method of Nunez (2001).[21] Briefly, cell suspensions were fixed and permeabilised by vigorous addition of nine volumes of ice-cold 70% (v/v) ethanol and stored at −20° C. for a minimum of 24 h, prior to analysis. Cells at a density of approximately 1×10$^6$ were re-suspended in 800 μl of propidium iodide staining solution (20 μg/ml propidium iodide and 200 μg/ml RNase A in PBS, pH 7.4) and incubated in the dark at room temperature for 30 min. The percentage of cells in the sub-$G_1$, $G_0/G_1$, S and $G_2/M$ phases of the cell cycle was determined over a range of concentrations and time points, and analysed from at least three independent experiments using Cell Quest™ software (Becton Dickinson).

Results cis-[Pt(NH$_3$)$_2$(malSAHA$_{-2H}$)]

Figure 12:
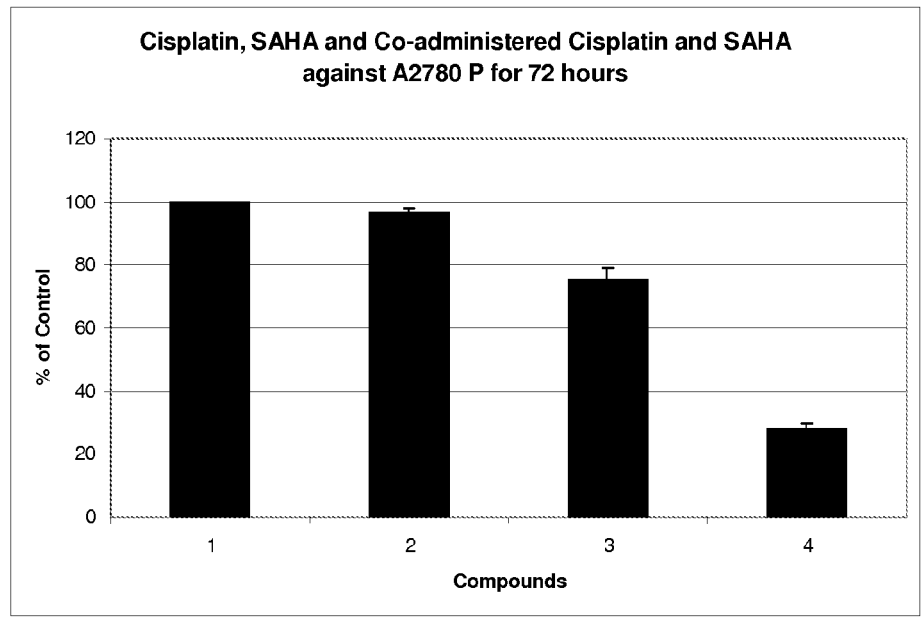
FIG. 12: Examination of cell proliferation by MTS assay. A2780 P cells were treated with no compound i.e. control (1), 0.75 µM Cisplatin (2), 2 µM SAHA (3) and 0.75 µM Cisplatin and 2 µM SAHA (4) for 72 hours.
Figure 13:
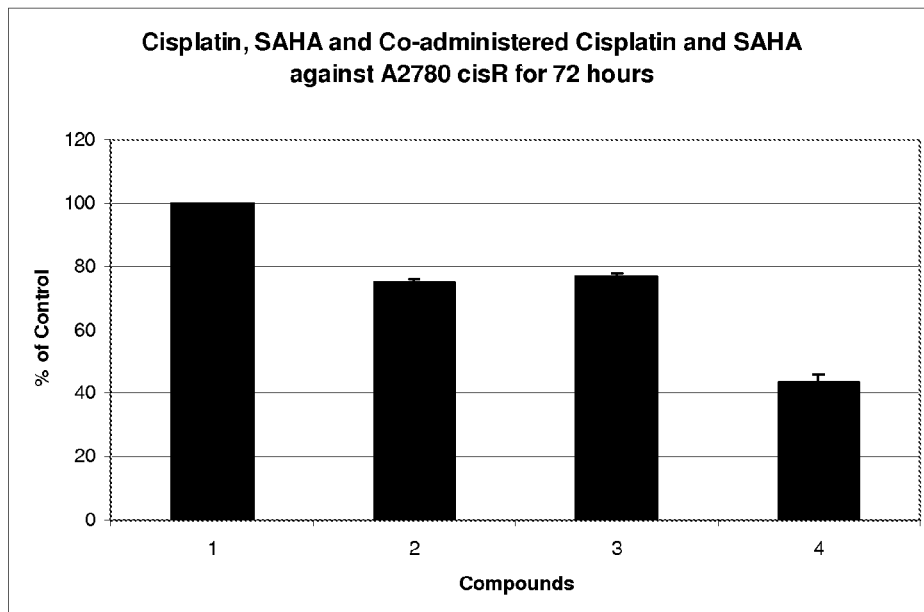
FIG. 13: Examination of cell proliferation by MTS assay. A2780 cisR cells were treated with no compound i.e. control (1), 10 µM Cisplatin (2), 2 µM SAHA (3) and 10 µM Cisplatin and 2 µM SAHA (4) for 72 hours.

(1.) An Investigation of the Potential Combinative Effects of Low Dose Cisplatin and Suberoylanilide Hydroxamic Acid (SAHA) Against the Ovarian Cancer Cell Line A2780 P and the Cisplatin Resistant Ovarian Cancer Cell Line A2780 cisR Initial experiment to show combination of SAHA and Cisplatin at single sub-toxic concentrations to see if there was any advantage in combining both into a single drug molecule. (FIG. 12 and FIG. 13)

(2.) Cytotoxicity

Figure 4:
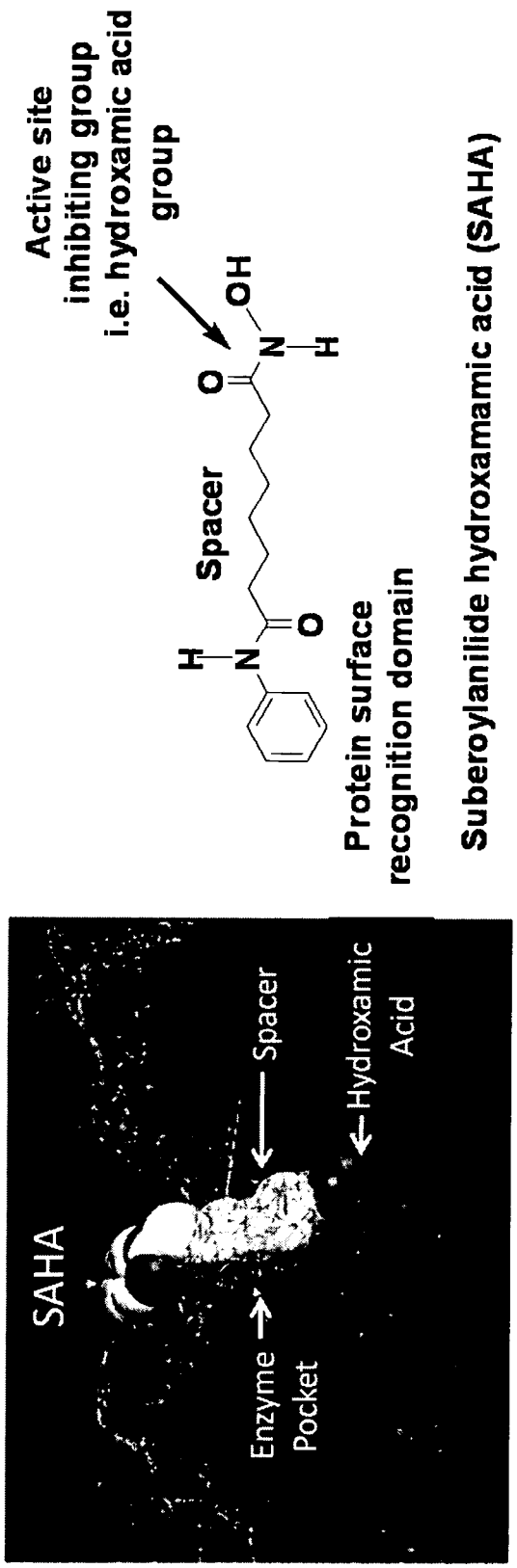
FIG. 4: Structure of suberoylanilide hydroxamic acid (SAHA) and structure of HDLP (homologue of mammalian HDAC with SAHA bound)[9].
Figure 5:
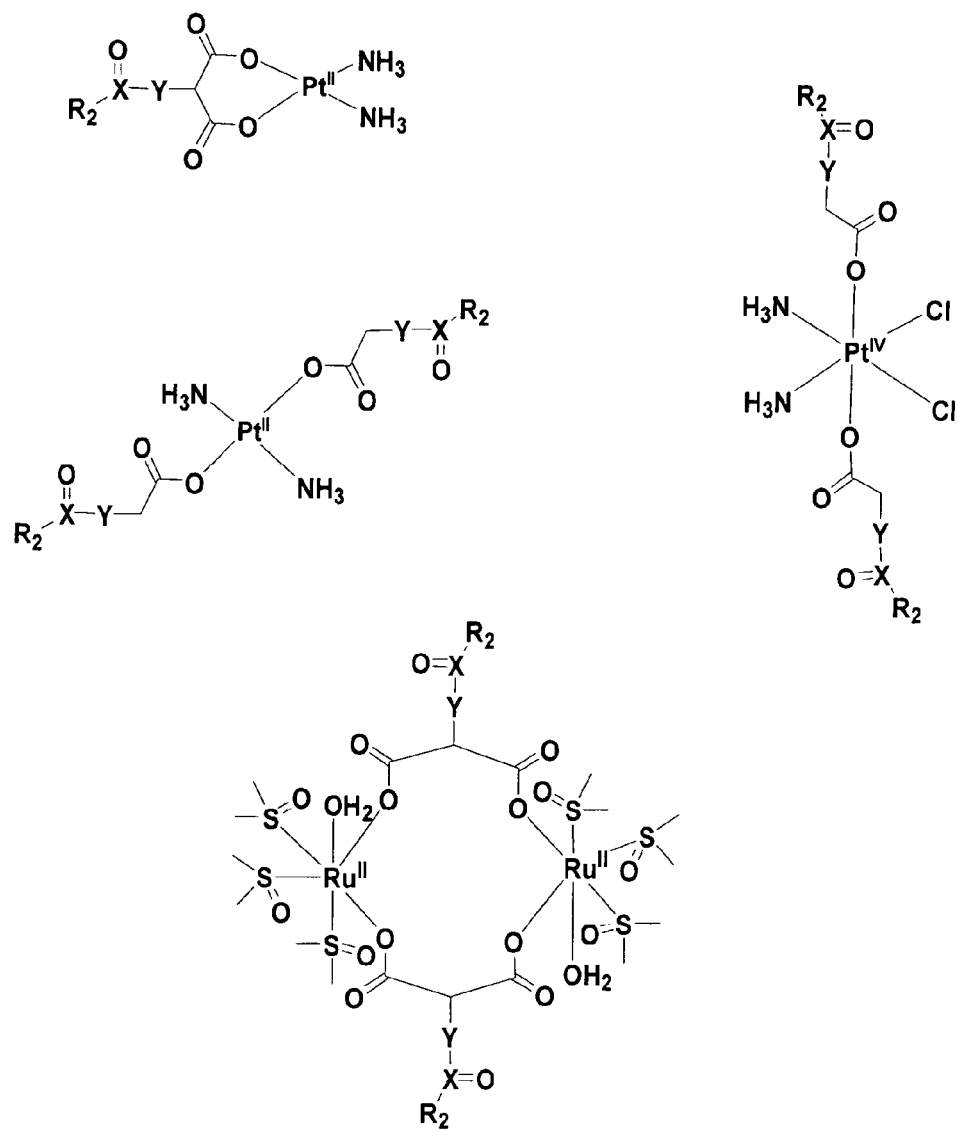
FIG. 5: Representative structures of mono- or bi-dendate or bridging X—(Y)$_n$—Z metal complexes
Figure 14:
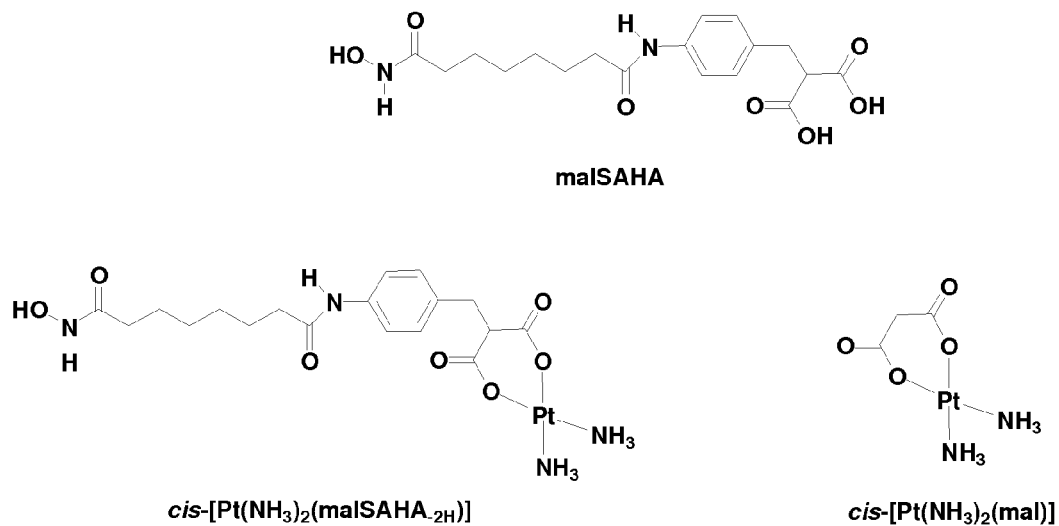
FIG. 14: Structures of malSAHA, cis-[Pt(NH$_3$)$_2$(malSAHA$_{-2H}$)] and cis-[Pt(NH$_3$)$_2$(mal)].
Figure 15:
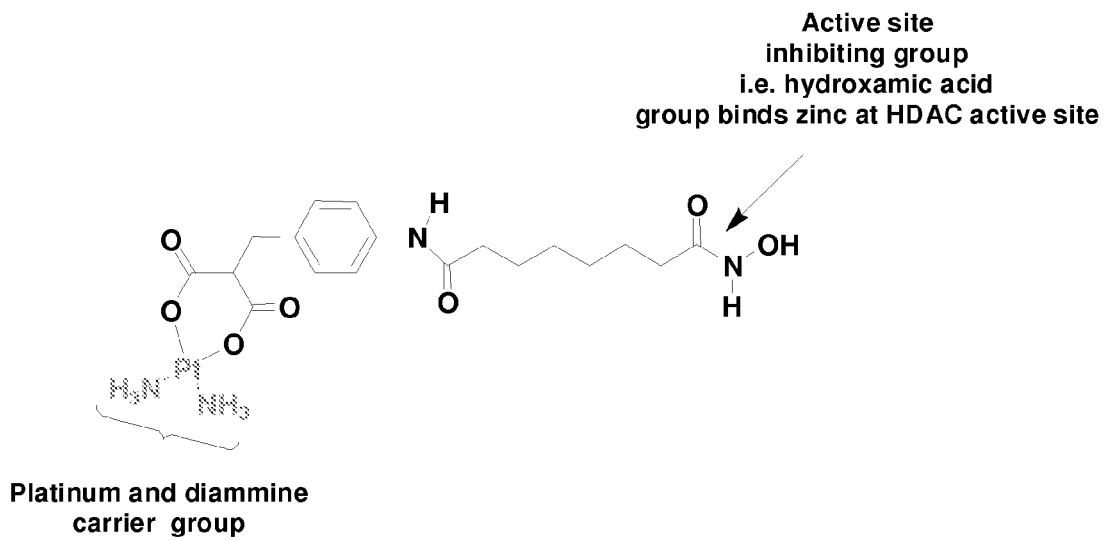
FIG. 15: Structure of cis-[Pt$^{II}$(NH$_3$)$_2$(malSAHA$_{-2H}$)].
Figure 16:
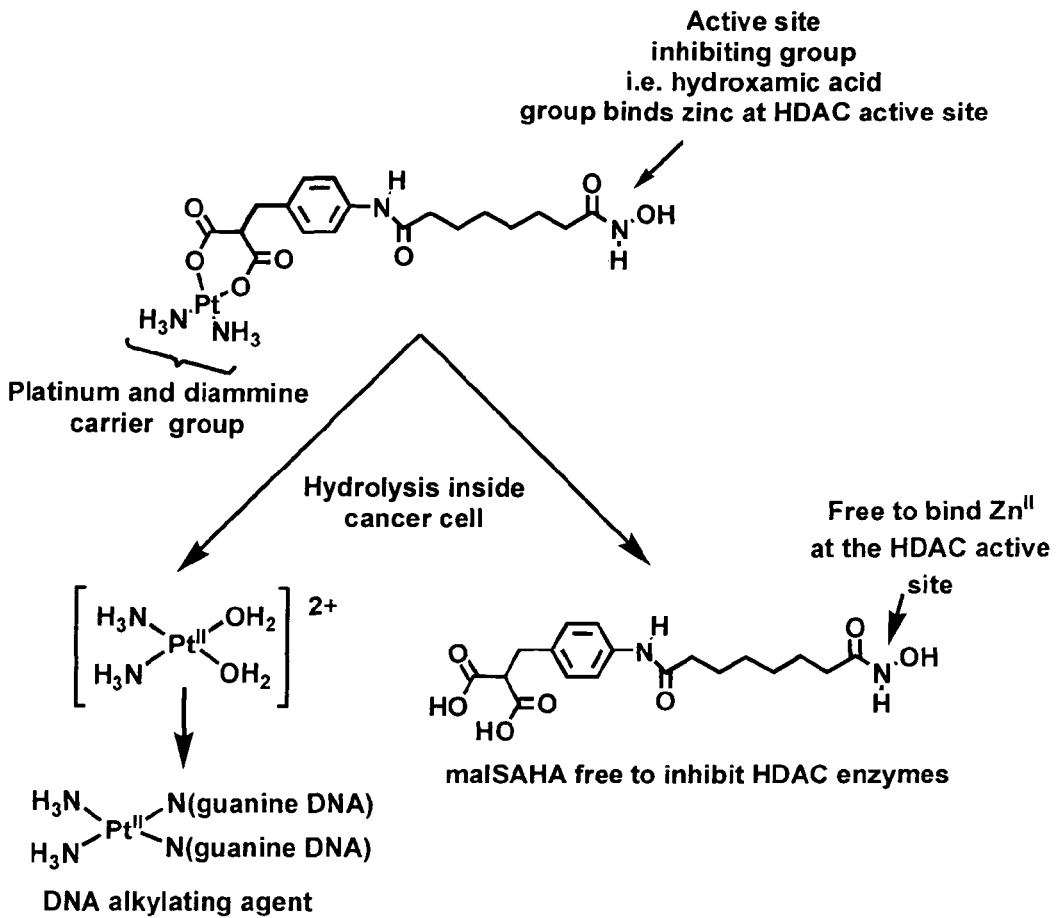
FIG. 16: Representation of hypothesis regarding hydrolysis of cis-[Pt$^{II}$(NH$_3$)$_2$(malSAHA$_{-2H}$)] inside cancer cells.

The cytotoxic activity of cis-[Pt(NH$_3$)$_2$(malSAHA$_{-2H}$)], FIG. 14, as well as standards cisplatin, FIG. 1, SAHA, FIG. 4 and cis-[Pt(NH$_3$)$_2$(mal)], FIG. 14, was determined against the non tumorigenic dermal fibroblast cell line (NHDF), cisplatin sensitive and cisplatin resistant ovarian cancer cell lines, A2780P and A2780 cisR respectively, the lung cancer cell line (A549), the breast cancer cell line (SKBR), the colon cancer cell line (SW480), the lymphoma cell line (CH1) and the liver cell lines (Hep-G2) as described previously. cis-[Pt$^{II}$(NH$_3$)$_2$(malSAHA$_{-2H}$)] displays selectivity for cancer cell lines over representative normal cell line NHDF.

TABLE 1

$IC_{50}$ values (μM) obtained for the test compounds against the non-tumorigenic human dermal fibroblast cell line (NHDF), the ovarian cancer cell lines (A2780 P and A2780 cisR), the lung cancer cell line (A549), the breast cancer cell line (SKBR), the colon cancer cell line (SW480), the lymphoma cell line (CH1) and the liver cell lines (Hep-G2) for 72 hours.

|  | cisplatin | SAHA | cis-[Pt$^{II}$(NH$_3$)$_2$(malSAHA$_{-2H}$)] | cis-[Pt(NH$_3$)$_2$(mal)] |
| --- | --- | --- | --- | --- |
| NHDF | 10 ± 1.8 | 4.5 ± 0.3 | 83 ± 7.6 | 48 ± 2.2 |
| A2780 P | 2.9 ± 0.1 | 3.5 ± 0.1 | 9 ± 3.1 | 16 ± 4.3 |
| A2780cisR | 28.5 ± 1.5 | 3.5 ± 0.1 | 70 ± 3.5 | 81 ± 5.8 |
| A549 | 6.3 ± 0.1 | 7.27 ± 1.7 | 12.7 ± 1.8 | 6.3 ± 20.1 |
| SKBR | 7.5 ± 1.2 | 1.7 ± 0.8 | 9.9 ± 1.8 | 14.6 ± 2.5 |
| SW480 | 8.0 ± 0.3 | 5.3 ± 1.8 | 13.4 ± 3.9 | 23.2 ± 1.5 |
| CH1 | 1.0 ± 0.5 | 1.2 ± 0.8 | 3.8 ± 0.5 | 2.5 ± 0.5 |
| Hep-G2 | 39.8 ± 3.5 | 4.0 ± 0.4 | 47.8 ± 4.0 | 44.5 ± 0.9 |

(3.) HDAC Inhibition Results

The ability of the test compounds, malSAHA and cis-[Pt(NH$_3$)$_2$(malSAHA$_{-2H}$)] as well as standards Trichostatin A, SAHA and cis-[Pt(NH$_3$)$_2$(mal)] to inhibit HDAC1 was investigated using Cayman's HDAC1 Inhibitor Screening Assay Kit as described previously. malSAHA and cis-[Pt(NH$_3$)$_2$(malSAHA$_{-2H}$)] inhibit HDAC1.[16]

TABLE 2

$IC_{50}$ values (nM) obtained for the test compounds against HDAC1 at 200 μM.

|  | $IC_{50}$ against HDAC I at 200 μM |
| --- | --- |
| Trichostatin A (control) | 8 nM |
| SAHA | 29 nM |
| malSAHA | 59.5 nM |
| cis-[Pt(NH$_3$)$_2$(malSAHA$_{-2H}$)] | 1143 nM |

(4) DNA Unwinding Experiment

Figure 17:
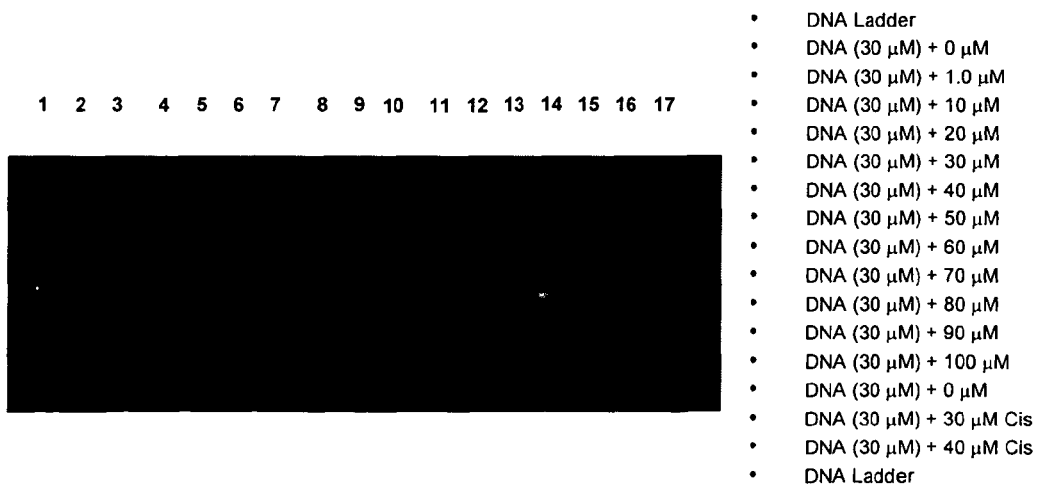
FIG. 17: Unwinding of closed circular supercoiled pUC19 plasmid DNA cis-[Pt$^{II}$(NH$_3$)$_2$(malSAHA$_{-2H}$)]. The top bands correspond to the open circular form of plasmid DNA and the bottom bands to closed, negatively supercoiled plasmid DNA.

Electrophoresis in native agarose gel of samples of pUC19 plasmid DNA incubated with a range of concentrations of cis-[Pt$^{II}$(NH$_3$)$_2$(malSAHA$_{-2H}$)] demonstrated that cis-[Pt$^{II}$(NH$_3$)$_2$(malSAHA$_{-2H}$)] can induce unwinding in negatively supercoiled pUC19 plasmid DNA and therefore bind DNA. This phenomenon was observed as a decrease in the rate of migration through agarose gel of samples of pUC19 plasmid DNA incubated with cis-[Pt$^{II}$(NH$_3$)$_2$(malSAHA$_{-2H}$)] as opposed to samples of pUC19 plasmid DNA alone, FIG. 17.[16]

(5) Determination of Pt Binding to DNA in Culture Cells

The ability of the Pt complexes to bind DNA in cultured cells was investigated as described previously. cis-[Pt$^{II}$(NH$_3$)$_2$(malSAHA$_{-2H}$)] binds DNA in cultured cells after 2 hours of cell treatment.

TABLE 3

DNA-bound Pt in SW480 (colon cancer cells) and CH1 (lymphoma cancer cells) exposed to 43 μM of Pt complexes after 2 hours of cell treatment.

| | SW480 (moles of Pt/μg of DNA) | CH1 (moles of Pt/μg of DNA) |
|---|---|---|
| cis-[Pt$^{II}$(NH$_3$)$_2$(malSAHA$_{-2H}$)] | $3.44 \cdot 10^{-5}$ | $1.45 \cdot 10^{-5}$ |
| cis-[Pt(NH$_3$)$_2$(mal)] | $1.25 \cdot 10^{-15}$ | $1.76 \cdot 10^{-15}$ |
| cisplatin | $38.5 \cdot 10^{-15}$ | $10.5 \cdot 10^{-15}$ |

Cellular Uptake of Pt

The cellular uptake of the Pt complexes in cancer cells was measured using flameless atomic absorption spectrophotometry (FAAS) and as described previously. cis-[Pt$^{II}$(NH$_3$)$_2$(malSAHA$_{-2H}$)] is taken up by cancer cells after 72 hours treatment and to a greater extent than cisplatin.

TABLE 4

Uptake (pmol Pt/2 × 10$^6$ cell) of Pt complexes at 10 μM and after 72 hours treatment into the following cells; SKBR (breast cancer cells), SW480 (colon cancer cells), A549 (lung cancer cells), A2780 P (ovarian cancer cells), and CH1 (lymphoma cancer cells).

| | | |
|---|---|---|
| cis-[Pt$^{II}$(NH$_3$)$_2$(malSAHA$_{-2H}$)] | SKBR | 6568 ± 312 |
| | SW480 | 5422 ± 222 |
| | A549 | 6419 ± 619 |
| | A2780 P | 5535 ± 865 |
| | CH1 | 1595 ± 158 |
| cis-[Pt(NH$_3$)$_2$(mal)] | SKBR | 488.15 ± 38.4 |
| | SW480 | 127.35 ± 27.4 |
| | A549 | 357.1 ± 47.1 |
| | A2780 P | 220.95 ± 10.95 |
| | CH1 | 282.6 ± 20.6 |
| Cisplatin | SKBR | 876.25 ± 70.55 |
| | SW480 | 391.95 ± 51.95 |
| | A549 | 614.85 ± 94.85 |
| | A2780 P | 612.25 ± 107.75 |
| | CH1 | 145.4 ± 21.8 | cis-[Pt(NH$_3$)$_2$(malBel$_{-2H}$)]

(1.) Cytotoxicity

The cytotoxicity of the test compounds against the ovarian cancer cell lines A2780 P and A2780 cisR (cisplatin sensitive and resistant respectively) for 72 hours was investigated. The cell lines were incubated for 72 h with the test compounds and the cell survival in the culture treated with the test compounds was evaluated as described previously. cis-[Pt$^{II}$(NH$_3$)$_2$(malBel$_{-2H}$)] displays selectivity for A2780 P cancer cell line over representative normal cell line NHDF and retains activity against A2780 cisR cell line (cisplatin resistant).

TABLE 5

IC$_{50}$ values (μM) obtained for cis-[Pt$^{II}$(NH$_3$)$_2$(malBel$_{-2H}$)] and standards against the non-tumorigenic human dermal fibroblast cell line (NHDF) and the ovarian cancer cell lines (A2780 P and A2780 cisR) for 72 hours.
IC$_{50}$ (μM) ± S.E.M.

| Cell line | Cisplatin | belinostat | Mal-bel | cis-[Pt$^{II}$(NH$_3$)$_2$(malBel$_{-2H}$)] |
|---|---|---|---|---|
| A2780P | 1.3 ± 0.1 | <1 | 45.8 ± 2.5 | 7.6 ± 0.3 |
| A2780CisR | 9.8 ± 1.0 | <1 | 32.1 ± 2.2 | 11.7 ± 0.9 |
| NHDF | 2.4 ± 0.6 | 3.0 ± 0.5 | 28.9 ± 1.4 | 33.9 ± 2.0 |

(2.) Determination of Pt Binding to DNA in Culture Cells

The ability of the Pt complexes to bind DNA in the ovarian cancer cell lines A2780 P and A2780 cisR (cisplatin sensitive and resistant respectively) was investigated as described previously. cis-[Pt$^{II}$(NH$_3$)$_2$(malBel$_{-2H}$)] binds DNA in A2780 P and A2780 cisR cancer cells and to a greater extent than cisplatin after 4 hours of cell treatment.

TABLE 6

DNA-bound Pt in the A2780 P and A2780 cis R (cisplatin sensitive and resistant ovarian cancer cells). exposed to 40 μM of Pt complexes after 4 hours of cell treatment.

| | A2780 P (moles of Pt/μg of DNA) | A2780 cisR (moles of Pt/μg of DNA) |
|---|---|---|
| cis-[Pt$^{II}$(NH$_3$)$_2$(malBel$_{-2H}$)] | $5,175 \cdot 10^{-15} \pm 27$ | $2,3855 \cdot 10^{-15} \pm 675$ |
| cisplatin | $200 \cdot 10^{-15} \pm 60$ | $665 \cdot 10^{-15} \pm 6$ |

(3.) Cellular Uptake Studies

The cellular uptake of the Pt complexes in A2780 P and A2780 cisR cancer cells was measured using flameless atomic absorption spectrophotometry (FAAS) and as described previously. cis-[Pt$^{II}$(NH$_3$)$_2$(malBel$_{-2H}$)] is taken up by cancer cells after 24 hours treatment.

TABLE 7

Uptake (pmol Pt/2 × 10$^6$ cell) of Pt complexes at 10 μM and after 24 hours treatment into the A2780 P and A2780 cisR (cisplatin sensitive and resistant ovarian cancer cells).

| | | |
|---|---|---|
| cis-[Pt$^{II}$(NH$_3$)$_2$(malBel$_{-2H}$)] | A2780 | 154 ± 10 |
| | A2780cisR | 42.3 ± 5.3 |
| Cisplatin | A2780 | 290 ± 35 |
| | A2780 | 98 ± 11 |

(4.) Inhibition of DNA Synthesis

Figure 18:
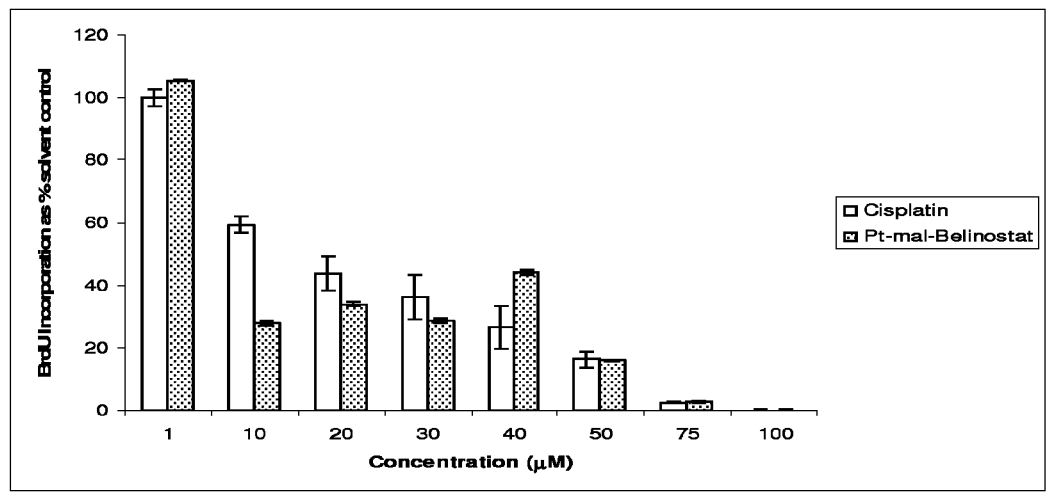
FIG. 18: The effects of cis-[Pt$^{II}$(NH$_3$)$_2$(malBel$_{-2H}$)] on DNA synthesis on A2780 P cells was determined using BrdU assays.
Figure 19:
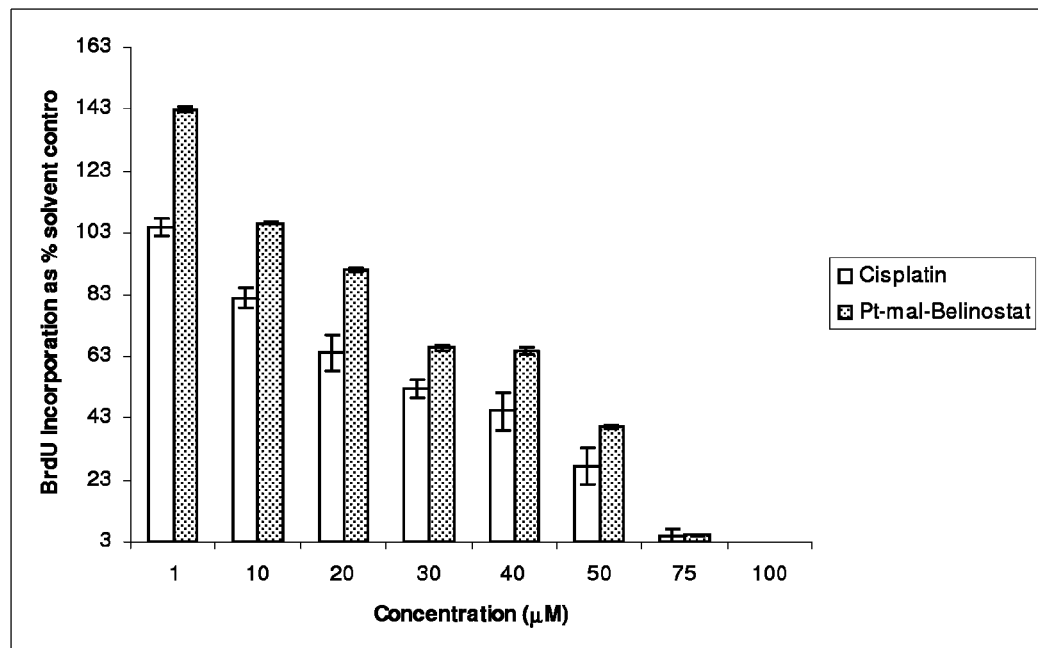
FIG. 19: The effects of cis-[Pt$^{II}$(NH$_3$)$_2$(malBel$_{-2H}$)] on DNA synthesis on A2780 cisR cells was determined using BrdU assays
Figure 20:
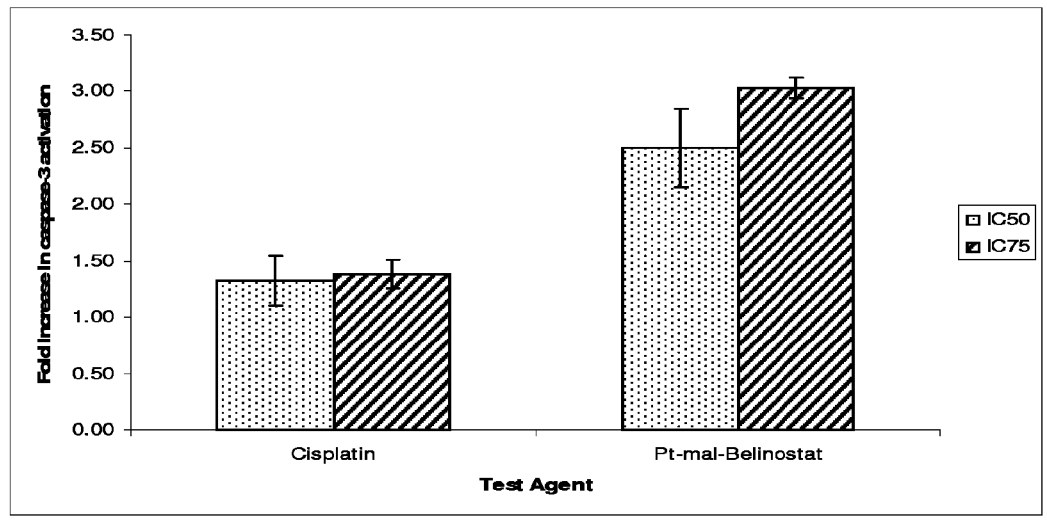
FIG. 20: The effects of cis-[Pt$^{II}$(NH$_3$)$_2$(malBel$_{-2H}$)] on caspase-3 activation was determined in A2780 P cells following 72 hr incubation. The fold-increase in caspase-3 activity was determined by comparison with that of the solvent control.
Figure 21:
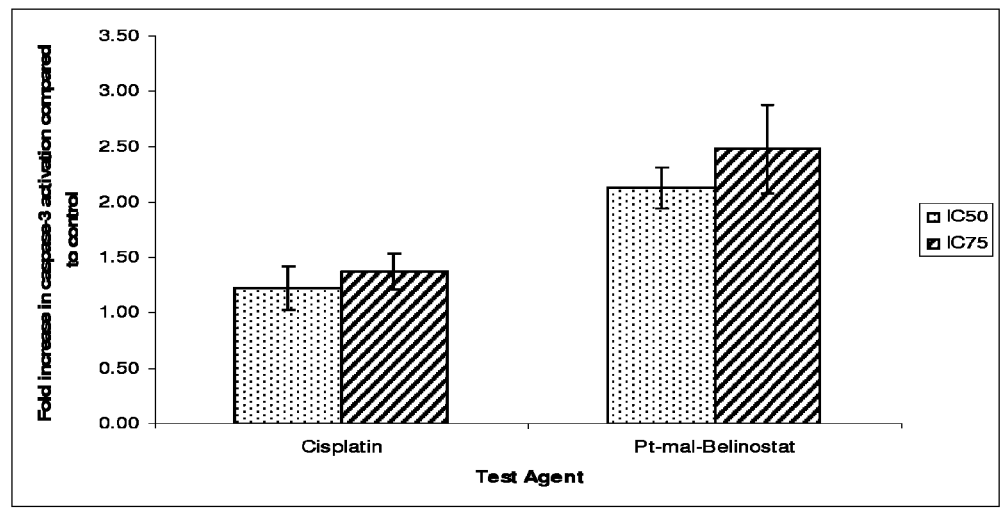
FIG. 21: The effects of cis-[Pt$^{II}$(NH$_3$)$_2$(malBel$_{-2H}$)] on caspase-3 activation was determined in A2780 cisR cells following 72 hr incubation. The fold-increase in caspase-3 activity was determined by comparison with that of the solvent control.
Figure 22:
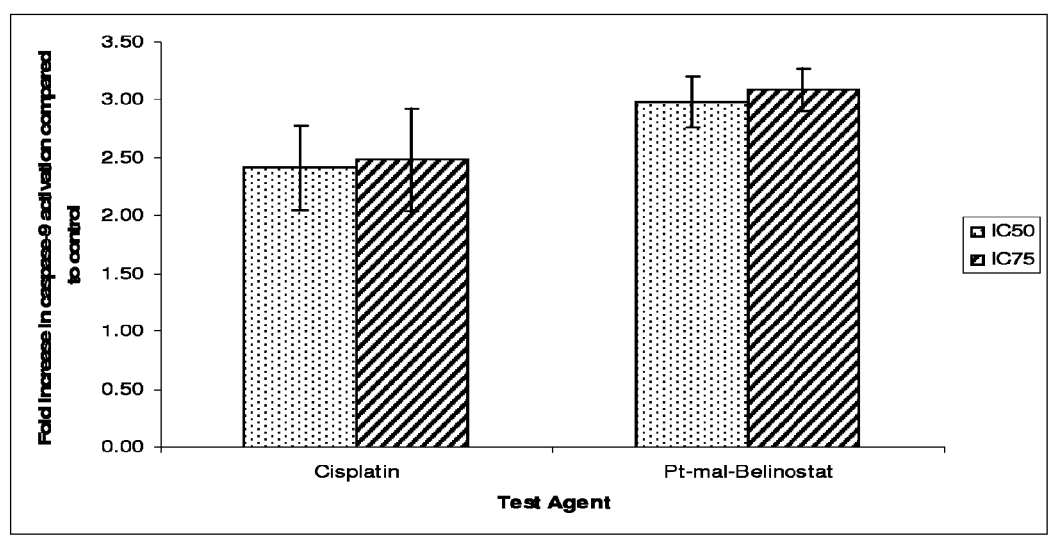
FIG. 22: The effects of cis-[Pt$^{II}$(NH$_3$)$_2$(malBel$_{-2H}$)] on caspase-9 activation was determined in A2780 P cells following 72 hr incubation. The fold-increase in caspase-9 activity was determined by comparison with that of the solvent control.
Figure 23:
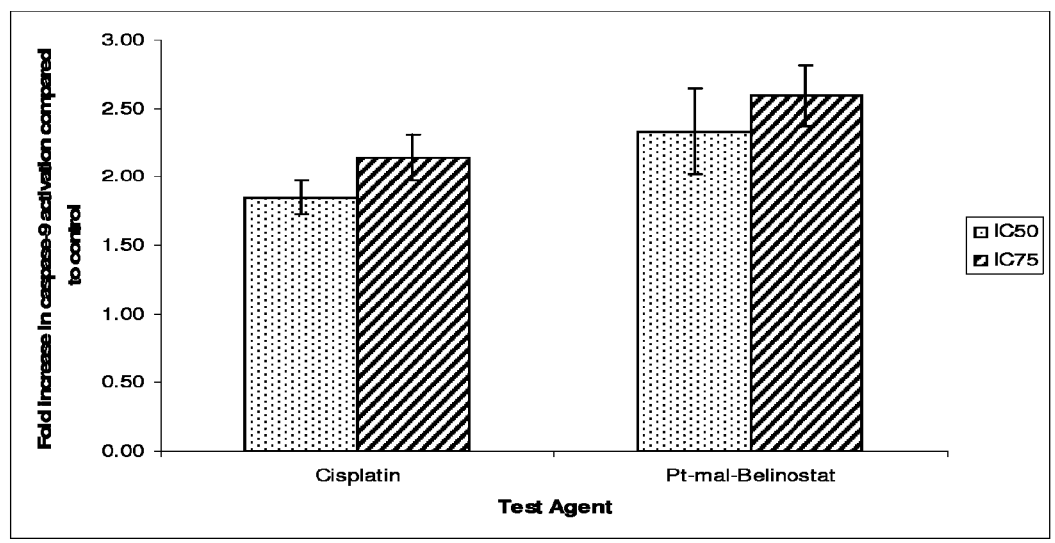
FIG. 23: The effects of cis-[Pt$^{II}$(NH$_3$)$_2$(malBel$_{-2H}$)] on caspase-9 activation was determined in A2780 cisR cells following 72 hr incubation. The fold-increase in caspase-9 activity was determined by comparison with that of the solvent control.
Figure 24:
FIG. 24: The effect of Cisplatin and cis-[Pt$^{II}$(NH$_3$)$_2$(malBel$_{-2H}$)] on the cellular morphology of A2780 P cells was assessed following 72 hr incubation using phase contrast microscopy (60× magnification).
Figure 24:
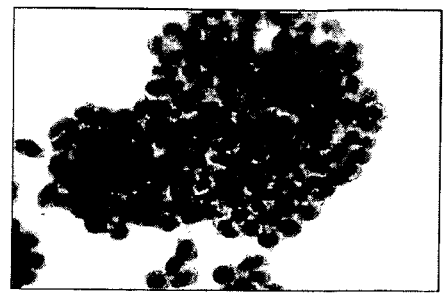
Figure 24:
Figure 24:
Figure 24:
Figure 24:
Figure 25:
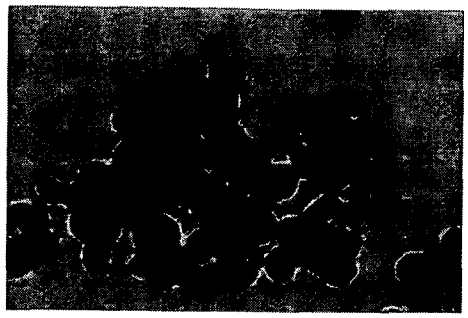
FIG. 25: The effect of Cisplatin and cis-[Pt$^{II}$(NH$_3$)$_2$(malBel$_{-2H}$)] on the cellular morphology of A2780 cisR cells was assessed following 72 hr incubation using phase contrast microscopy (60× magnification).
Figure 25:
Figure 25:
Figure 25:
Figure 25:
Figure 25:
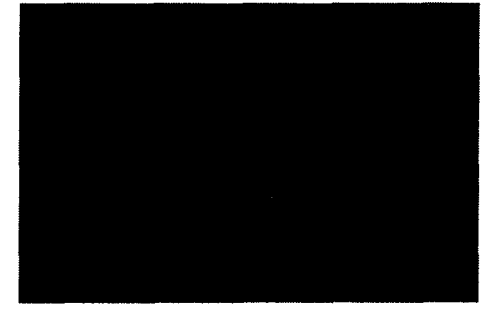
Figure 26:
FIG. 26: The effect of cisplatin and cis-[Pt$^{II}$(NH$_3$)$_2$(malBel$_{-2H}$)] on the cellular morphology of A2780 P cells was assessed following 72 hr incubation using DAPI staining and fluorescence microscopy (60× magnification).
Figure 26:
Figure 26:
Figure 26:
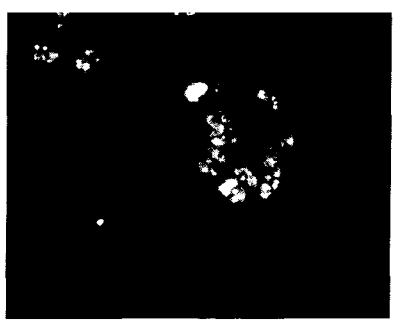
Figure 26:
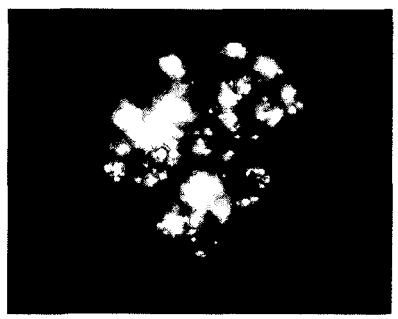
Figure 26:
Figure 27:
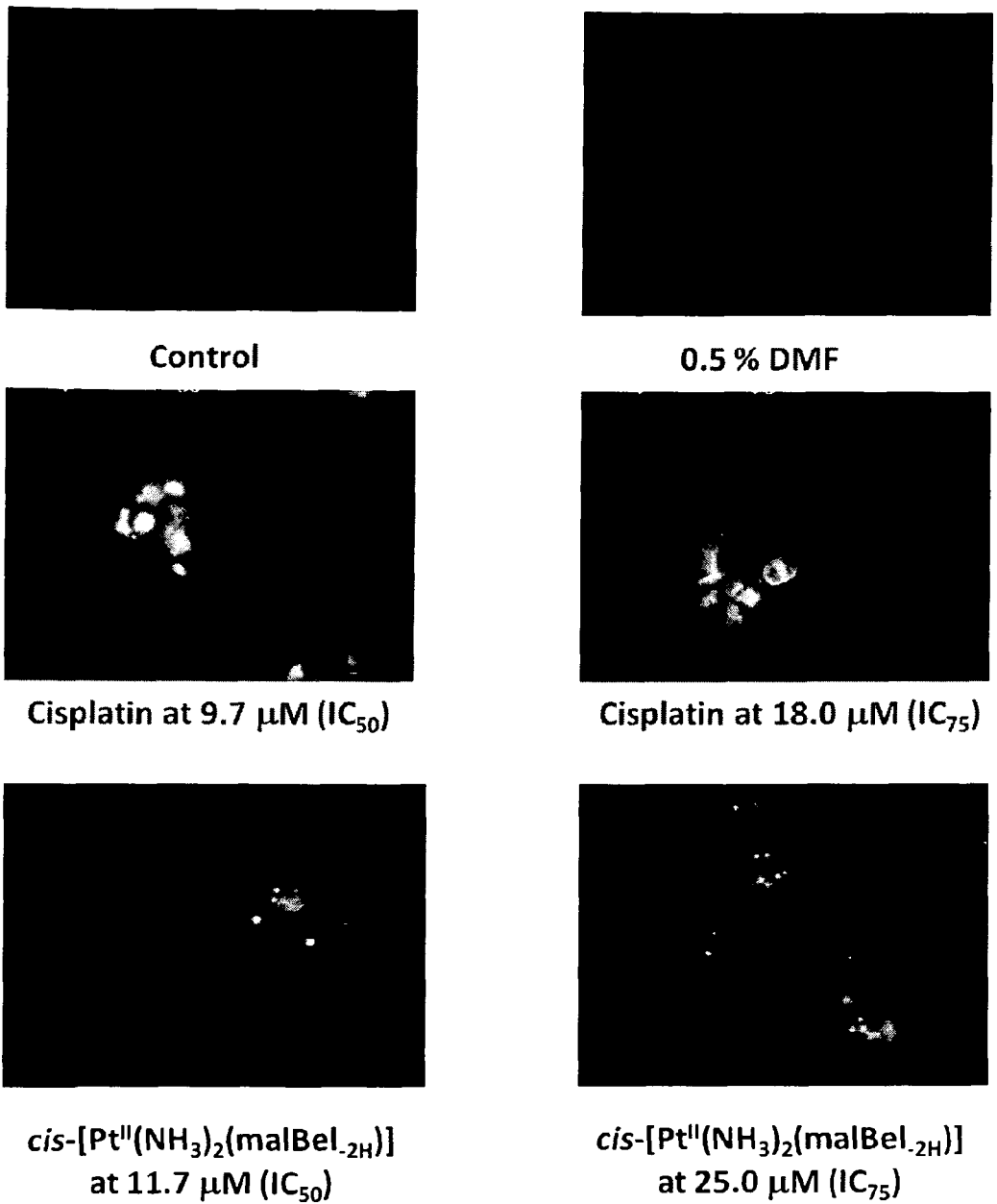
FIG. 27: The effect of cisplatin and cis-[Pt$^{II}$(NH$_3$)$_2$(malBel$_{-2H}$)] on the cellular morphology of A2780 cisR cells was assessed following 72 hr incubation using DAPI staining and fluorescence microscopy (60× magnification).
Figure 28:
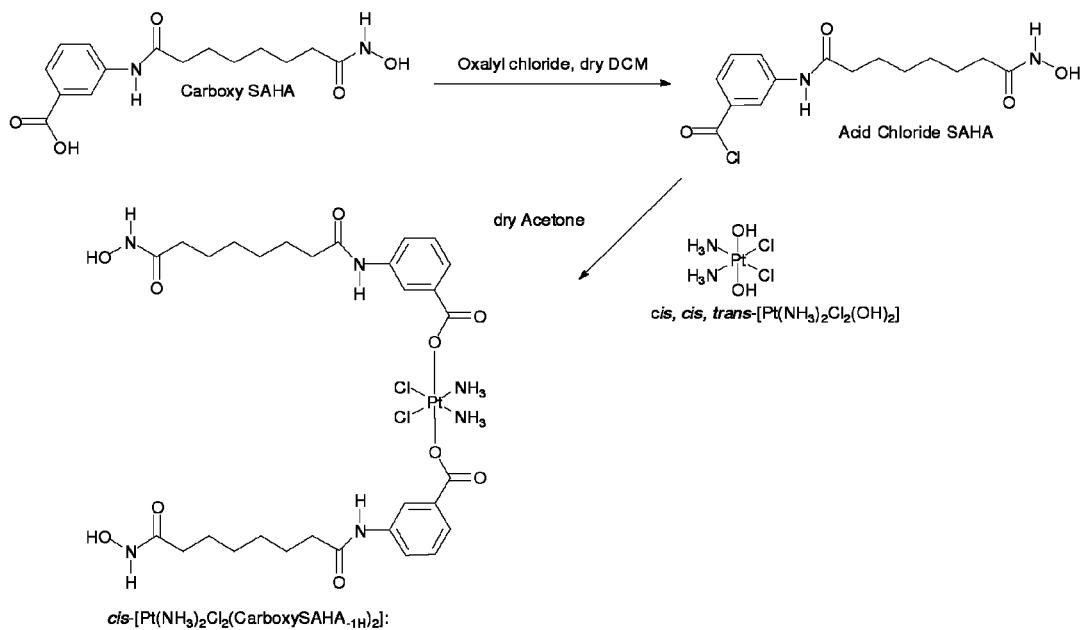
FIG. 28 Proposed synthesis of the Pt(IV) carboxySAHA complex, cis-[Pt(NH$_3$)$_2$Cl$_2$(carboxySAHA$_{-1H}$)$_2$].
Figure 29:
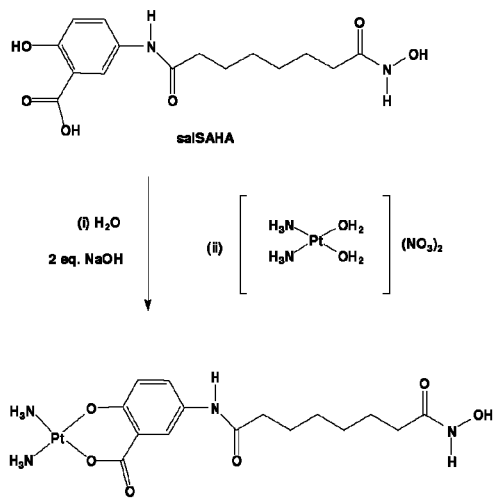
FIG. 29 Proposed synthesis of the Pt(II) salSAHA complex, cis-[Pt(NH$_3$)$_2$(salSAHA$_{-2H}$)].

To determine the events responsible for the observed reduction in cellular proliferation of A2780 P and A2780 cisR cancer cells, the effect of cis-[Pt$^{II}$(NH$_3$)$_2$(malBel$_{-2H}$)] on DNA synthesis was investigated using BrdU incorporation assays. cis-[Pt$^{II}$(NH$_3$)$_2$(malBel$_{-2H}$)] caused dose-dependant decrease in DNA synthesis, as seen in FIGS. 18 and 19.

(5.) Caspase Assays to Detect Cell Death

Caspase-3 is known to be one of the main executioner/effector caspases which is activated by caspase-9. The results presented in FIGS. 20-23 show an increase in both Caspase-3 and -9 activities following 72 hr incubation of A2780 P and A2780 cisR cancer cells lines with cis-[Pt$^{II}$(NH$_3$)$_2$(malBel$_{-2H}$)] at concentrations equal to the IC$_{50}$ and IC$_{75}$ and at 72 hr.

(6.) Morphological Analysis

The effect on A2780 P and A2780 cisR cellular morphology and the integrity of DNA from A2780 P and A2780 cisR cells treated with cisplatin and cis-[Pt$^{II}$(NH$_3$)$_2$(malBel$_{-2H}$)] was investigated using Methylene Blue and Eosin staining and DAPI staining, respectively as shown FIGS. 24-27.

Exposure of the cells to Pt complexes at concentrations equal to their IC$_{50}$ and IC75 and for 72 hr, caused considerable thinning of the monolayer, attenuation of cells and the nuclei to be intensively stained and fragmented. These results suggest that cell death was via apoptosis.

(7.) Effects of cis-[Pt$^{II}$(NH$_3$)$_2$(malBel$_{-2H}$)] on Cell Cycle Progression The effect of Pt complexes on cell cycle events was examined for evidence of apoptotic cell death. A2780 P cells were exposed to cisplatin and cis-[Pt$^{II}$(NH$_3$)$_2$(malBel$_{-2H}$)] for 72 hr and the percentage of cells entering each phase of the cell cycle was determined. The cell cycle progression table below shows a disruption in phase progression and a dose dependent increase in sub-G$_1$ accumulation compared to control cells, indicative of apoptosis.

TABLE 8

Cell cycle progression tables for Pt on A2780 P ovarian cancer cells.

| 72 hr | % Sub-G$_1$ ± S.E.M. | % G$_0$/G$_1$ ± S.E.M. | % S ± S.E.M. | % G$_2$/M ± S.E.M. |
|---|---|---|---|---|
| CTRL | 26.62 ± 0.46 | 41.73 ± 0.65 | 4.79 ± 0.20 | 12.26 ± 0.36 |
| DMF CTRL (0.5% v/v) | 20.02 ± 0.59 | 47.90 ± 0.65 | 5.23 ± 0.16 | 13.56 ± 0.46 |
| Cisplatin IC$_{50}$ (1.3 μM) | 64.16 ± 0.74 | 18.58 ± 0.58 | 5.33 ± 0.13 | 5.44 ± 0.04 |
| Cisplatin IC$_{75}$ (5.0 μM) | 61.81 ± 0.39 | 20.88 ± 0.14 | 5.81 ± 0.30 | 4.73 ± 0.13 |
| cis-[Pt(NH3)2(malBel$_{-2H}$)] IC$_{50}$ (7.6 μM) | 60.86 ± 0.26 | 16.16 ± 0.88 | 7.21 ± 0.11 | 7.91 ± 0.03 |
| cis-[Pt(NH3)2(malBel$_{-2H}$)] IC$_{75}$ (12.0 μM) | 67.67 ± 0.43 | 11.75 ± 0.17 | 5.59 ± 0.36 | 8.04 ± 0.72 |

The invention is not limited to the embodiments hereinbefore described which may be varied in construction and detail without departing from the spirit of the invention.

REFERENCES

1. M. Galanski, M. A. Jakupec and B. K. Keppler, *Curr. Med. Chem.*, 2005, 12, 2075-2094.
2. L. Kelland, *Nat. Rev.*, 2007, 7, 573-584.
3. O. A. Botrugno, F. Santoro and S. Minucci, *Cancer Lett.*, 2009, 280, 134-144.
4. H. M. Prince, M. J. Bishton and R. W. Johnstone, *Future Oncol.*, 2009, 5, 601-612.
5. J. E. Bolden, M. J. Peart and R. W. Johnstone, *Nat. Rev. Drug Discov.*, 2006, 5, 769-784.
6. S. Minucci and P. G. Pelicci, *Nat. Rev. Cancer*, 2006, 6, 38-51.
7. S. Cang, Y. Ma and D. Liu, *J. Hematol. Oncol.*, 2009, 2:22.
8. M. Dokmanovic, G. Perez, W. Xu, L. Ngo, C. Clarke, R. B. Parmigiani and P. A. Marks, *Mol. Cancer Ther.*, 2007, 6, 2525-2534.
9. K. Ozaki, F. Kishikawa, M. Tanaka, T. Sakamoto, S. Tanimura and M. Kohno, *Cancer Sci.*, 2008, 99, 376-384.
10. W. Rasheed, M. J. Bishton, R. W. Johnstone and H. M. Prince, *Expert Rev. Anticancer Ther.*, 2008, 8, 413-432.
11. A. J. Frew, R. W. Johnstone and J. E. Bolden, *Cancer Lett.*, 2009, 280, 125-133.
12. A. Mai, M. Esposito, G. Sbardella and S. Massa, *OPPI Briefs*, 2001, 33, 391-394.
13. S. C. Dhara, *Indian J. Chem.*, 1970, 8, 193-194.
14. A. H. Cory, T. C. Owen, J. A. Barltrop and J. G. Cory, *Cancer Commun.*, 1991, 3, 207-212.
15. T. L. Riss and R. A. Moravec, *Mol. Biol. Cell*, 1992, 3, 184a.
16. D. Griffith, M. P. Morgan and C. J. Marmion, *Chem. Commun.*, 2009, 6735-6737.
17. A. Halámiková, P. Heringová, J. Kaspárková, F. P. Intini, G. Natile, A. Nemirovski, D. Gibson and V. Brabec, *J. Inorg. Biochem.*, 2008, 102, 1077-1089.
18. T. Portsmann, T. Ternyck and S. Aveameas, *J. Immunol. Meth.*, 1985, 82, 169-179.
19. R. I. Freshney, *Culture of animal cells; a manual of basic techniques.*, 3 edn., Wiley-Liss, New York, 1994.
20. M. M. Compton, *Cancer Metastasis Rev.*, 1992, 11, 105-112.
21. R. Nunez, *Curr. Issues Mol. Biol.*, 2001, 3, 67-70.

The invention claimed is:

1. A metal complex comprising a histone deacetylase (HDAC) inhibitor coordinated to a DNA-binding heavy metal ion and having the general structure:

[X—Y—Z-M$^{n+}$]$^{P+}$.B in which:

X is a HDAC inhibitor having a terminal hydroxamate group;

Y is a spacer group or is absent;

Z is a mono-dentate, bi-dentate, bridging or chelating oxygen donor linker;

M$^{n+}$ is a DNA-binding heavy metal ion selected from platinum, palladium, ruthenium, osmium, gold, iron and copper, in which the heavy metal ion is coordinated to one or more ligands to complete its coordination sphere;

P+ designates the charge on the complex ion, which may be positive, negative or absent; and B is a counterion or is absent.

2. A metal complex as claimed in claim 1 in which the DNA-binding heavy metal ion is selected from platinum, palladium, ruthenium, and osmium.

3. A metal complex as claimed in claim 1 in which [X—Y—Z-M$^{n+}$]$^{P+}$ has a general formula VII, VIII or IX:

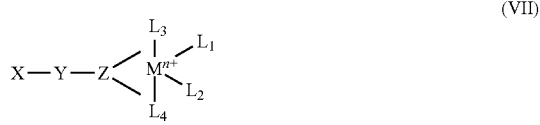

(VII)

(VIII)

-continued

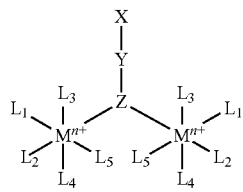
(IX)

in which:
Z is a bidentate O,O' linker (VII) or a monodentate O linker (VIII) or a bridging linker (IX); and
$L_1$ to $L_5$ are each, independently, absent or a substituent selected from the group consisting of: ammonia; a mono- or multi-dentate or bridging X—Y—Z; a primary amine; a secondary amine; a non-planar heterocyclic aliphatic amine or a heterocyclic aromatic amine; a sulphur donor ligand; a phosphorous donor ligand; a halogen; an oxygen donor ligand; and a multidentate chelating ligand formed between two or more of $L_1$-$L_5$.

4. A metal complex as claimed in claim 3 in which Z is a bidentate O,O' linker, $M^{n+}$ is square planar $Pt^{2+}$ or $Pd^{2+}$ in cis geometry, $L_3$ and $L_4$ are absent, and $L_1$ and $L_2$ are each, independently, represented by a group selected from: an amine which can be the same or different (or joined together to form a bidentate chelating ligand) selected from ammonia, a primary amine, a secondary amine, a non-planar heterocyclic aliphatic amine or a heterocyclic aromatic amine; a sulphur donor ligand; a phosphorous donor ligand; a halogen; an oxygen donor ligand; or X—Y—Z—.

5. A metal complex as claimed in claim 3 in which Z is a bidentate O,O' linker, $M^{n+}$ is octahedral $Pt^{4+}$, $Pd^{4+}$, $Ru^{3+}$, $Ru^{2+}$, $Os^{3+}$ or $Os^{2+}$, and $L_1$-$L_4$ are each, independently, represented by a group selected from: X—Y—Z—; an amine which can be the same or different (or joined together to form a bi- or multi-dendate chelating ligand) selected from ammonia, a primary amine, a secondary amine; a non-planar heterocyclic aliphatic amine or a heterocyclic aromatic amine; a sulphur donor ligand; or a phosphorous donor ligand; a halogen; and an oxygen donor ligand.

6. A metal complex as claimed in claim 3 in which Z is a monodentate O linker, $M^{n+}$ is square planar $Pt^{2+}$ or $Pd^{2+}$ in cis or trans geometry, $L_3$ and $L_4$ are absent, and $L_1$, $L_2$, and $L_5$ are each, independently, represented by a group selected from: an amine which can be the same or different (or joined together to form a bi- or tri-dendate chelating ligand) selected from ammonia, a primary amine, a secondary amine, a non-planar heterocyclic aliphatic amine or a heterocyclic aromatic amine; a sulphur donor ligand; a phosphorous donor ligand; a halogen; an oxygen donor ligand; and X—Y—Z—.

7. A metal complex as claimed in claim 3 in which Z is a monodentate ligand, $M^{n+}$ is octahedral $Pt^{4+}$, $Pd^{4+}$, $Ru^{3+}$, $Ru^{2+}$, $Os^{3+}$, or $Os^{2+}$, and $L_1$-$L_5$ are each, independently, represented by a group selected from: at least one X—Y—Z—; an amine which can be the same of or different (or joined together to form a bi-, tri- or tetra-dendate chelating ligand) selected from ammonia, a primary amine, a secondary amine, a non-planar heterocyclic aliphatic amine or a heterocyclic aromatic amine; a sulphur donor ligand; a phosphorous donor ligand; a halogen; and an oxygen donor ligand.

8. A metal complex as claimed in claim 1 in which $[X—Y—Z-M^{n+}]^{P+}$ has a general formula selected from the group consisting of:

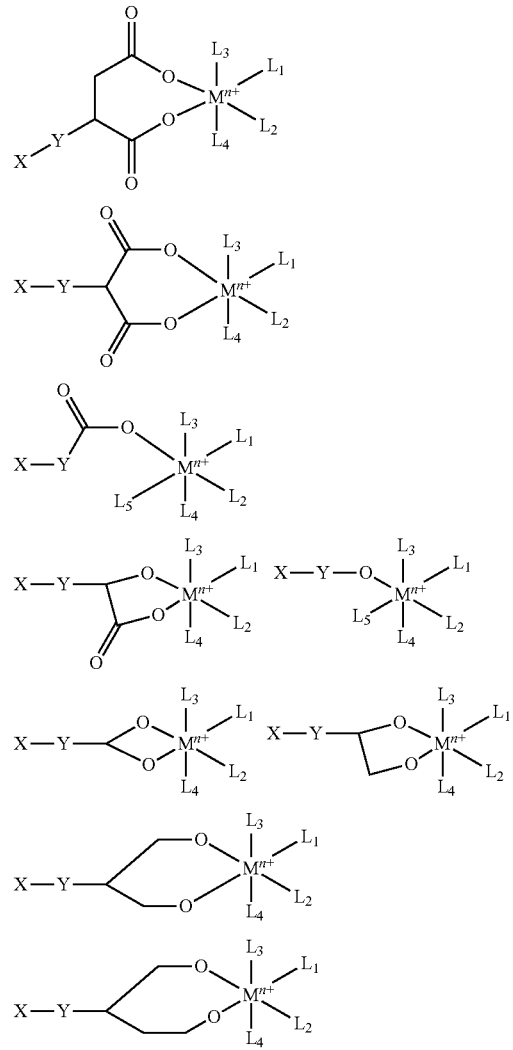

9. A metal complex as claimed in claim 1 in which $[X—Y—Z-M^{n+}]^{P+}$ has a general formula selected from the group consisting of:

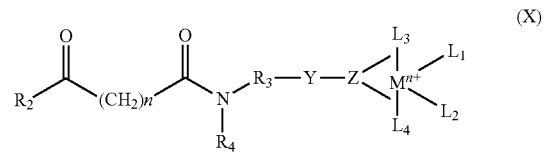
(X)

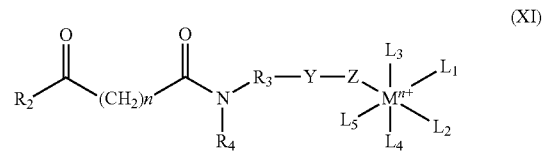
(XI)

-continued

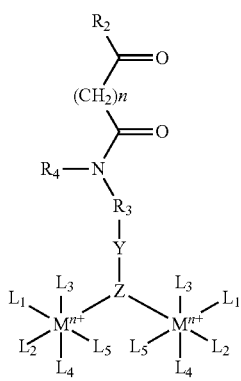

(XII)

in which:

R₃ is a substituted or unsubstituted, branched or unbranched alkylene, alkenylene, cycloalkylene, aryl, acyl, heteroaryl, arylalkylene, heteroarylalkylene, aromatic polycycles non-aromatic polycycles, mixed aryl and non-aryl polycycles, polyheteroaryl, non-aromatic polyheterocycles, or mixed aryl and non-aryl polyheterocycles;

R₄ is a hydrogen, hydroxyl, a substituted or unsubstituted, branched or unbranched alkyl, a $C_1$-$C_6$ alkyl, alkenyl, cycloalkyl, a $C_4$-$C_9$ cycloalkyl, aryl, acyl, heteroaryl, arylalkyl, heteroarylalkyl, aryloxy, alkyloxy, arylalkyloxy, aromatic polycycles, non-aromatic polycycles, mixed aryl and non-aryl polycycles, polyheteroaryl, non-aromatic polyheterocycles, or mixed aryl and non-aryl polyheterocycles;

R₂ is a hydroxylamino group; and n is an integer from 5 to 8.

10. A metal complex accordingly to claim 9 and selected from the group consisting of:

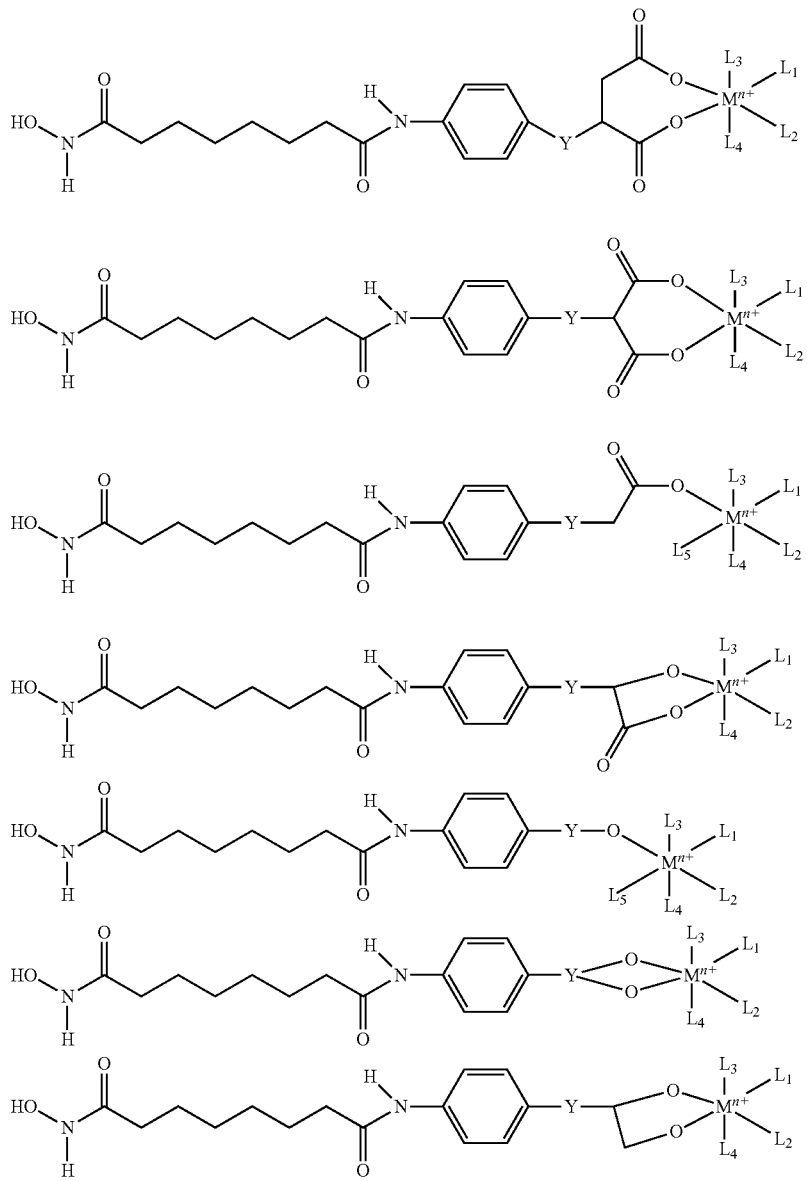

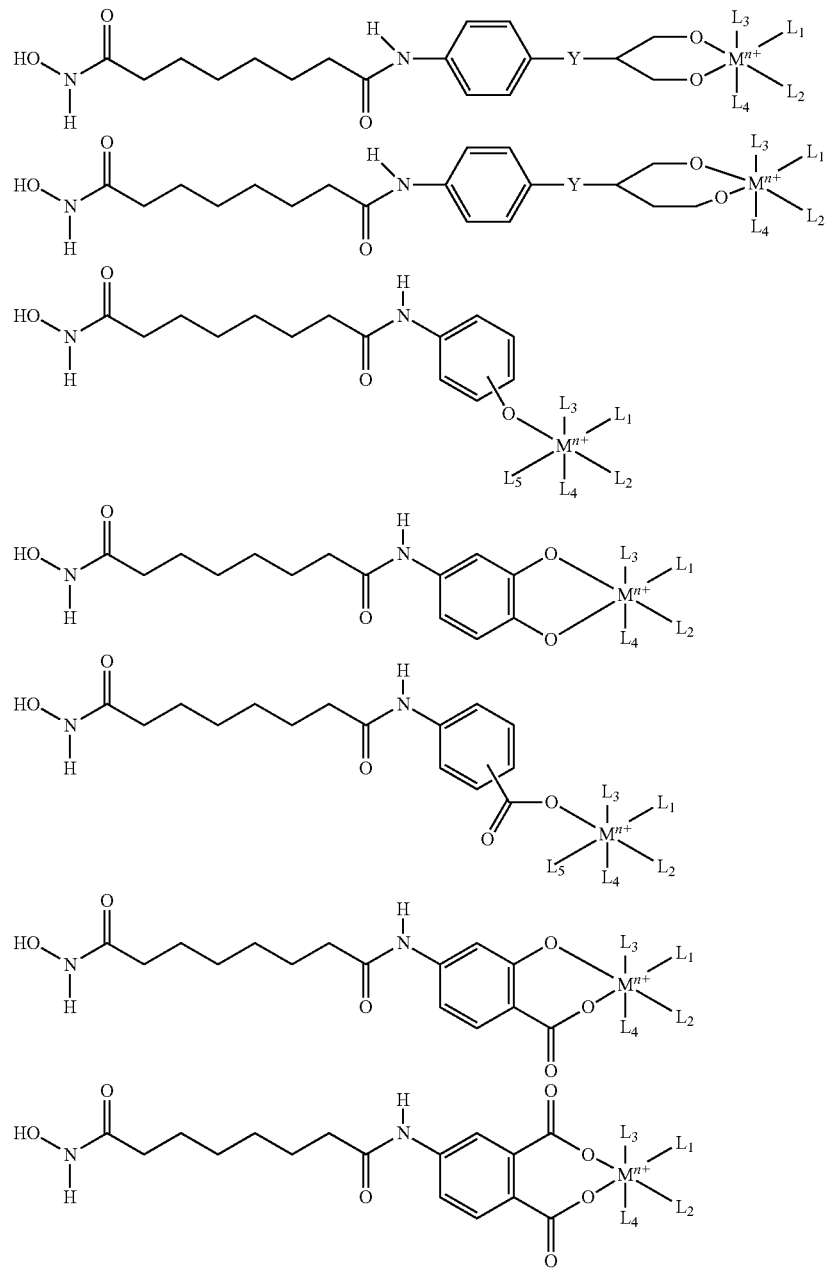
11. A metal complex as claimed in claim 1 in which $[X{-}Y{-}Z{-}M^{n+}]^{P+}$ has a general formula XIII or XIV or XV:
-continued
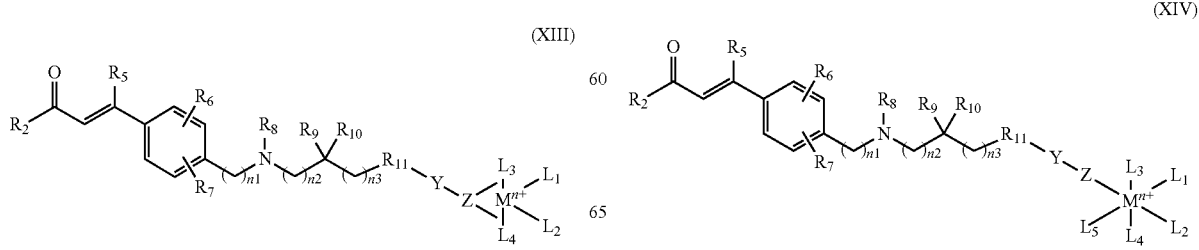

-continued

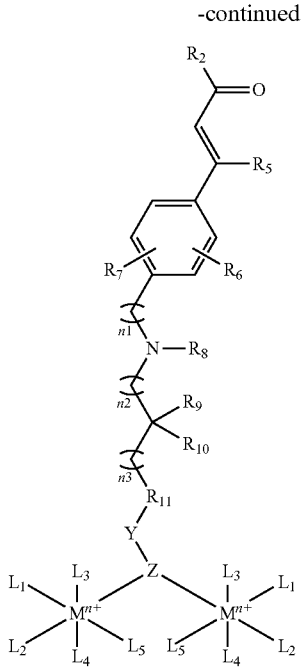

(XV)

in which:

$R_2$, Y, Z, $M^{n+}$, and $L_1$ to $L_5$ are as defined above;
$R_5$ is H, halo, or a straight chain $C_1$-$C_6$ alkyl;

$R_6$ and $R_7$ are the same or different and independently selected from the group consisting of H, halo, $C_1$ to $C_4$ alkyl, $NO_2$, $C(O)R_5$, $OR_{12}$, $SR_{12}$, CN, and $NR_{13}R_{14}$;

$R_8$ is H, $C_1$ to $C_{10}$ alkyl, $C_4$ to $C_9$ cycloalkyl, $C_4$ to $C_9$ heterocycloalkyl, $C_4$ to $C_9$ heterocycloalkylalkyl, cycloalkylalkyl, aryl, heteroaryl, arylalkyl, heteroarylalkyl, —$(CH_2)_nC(O)R_6$, —$(CH_2)_nO(O)R_6$, amino acyl, or HON—C(O)—CH=C($R_1$)-aryl-alkyl;

$R_9$ and $R_{10}$ are the same or different and independently selected from the group consisting of H, $C_1$-$C_6$ alkyl, acyl and acylamino, or $R_9$ and $R_{10}$ together with the carbon to which they are bound represent C=O, C=S, or $R_8$ together with the nitrogen to which it is bound and $R_9$ together with the carbon to which it is bound form a $C_4$-$C_9$ heterocycloalkyl, a heteroaryl, a polyheteroaryl, a non-aromatic polyheterocycle, or a mixed aryl and non-aryl polyheterocycle ring;

$R_{11}$ is selected from the group consisting of $C_1$-$C_6$ alkylene, $C_4$-$C_9$ cycloalkylene, $C_4$-$C_9$ heterocycloalkylene, acyl, aryl, heteroaryl, arylalkylene, heteroarylalkylene, aromatic polycycles, non-aromatic polycycles, mixed aryl and non-aryl polycycles, polyheteroaryl, non-aromatic polyheterocycles, and mixed aryl and non-aryl polyheterocycles;

$R_{12}$ is selected from the group consisting of $C_1$-$C_4$ alkyl, and C(O)-alkyl;

$R_{13}$ and $R_{14}$ are the same or different and independently selected from the group consisting of H, $C_1$-$C_4$ alkyl, and —C(O)-alkyl; and $n_1$, $n_2$ and $n_3$, independently, are 0-6, when $n_1$ is 1-6, each carbon atom is optionally and independently substituted with $R_9$ and/or $R_{10}$.

12. A metal complex as claimed in claim 11 in which [X—Y—Z-$M^{n+}$]$^{P+}$ has a general formula XVI, XVII or XVIII:

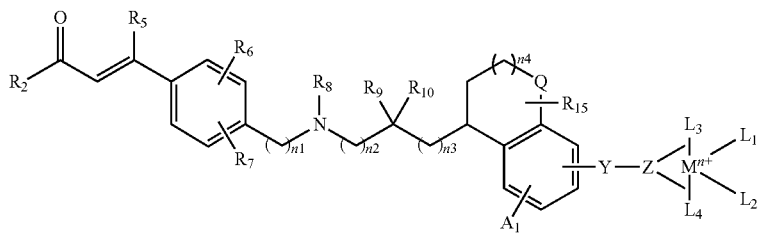

(XVI)

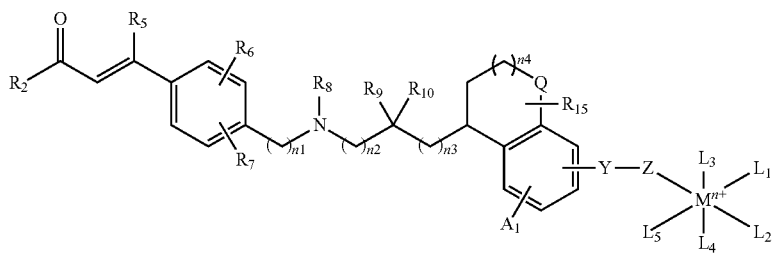

(XVII)

51

-continued (XVIII)

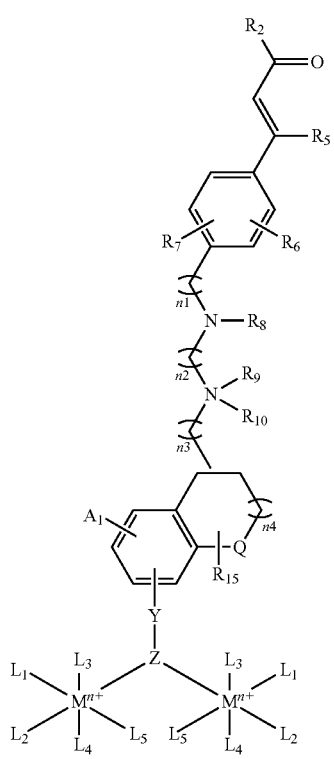

in which:
R$_5$, R$_6$, R$_7$, R$_8$, R$_9$, R$_{10}$, Y, Z and n$_1$ to n$_3$ are as defined above;
n$_4$ is 0, 1 or 2;
R$_{11}$ is

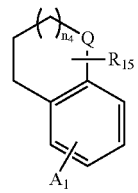

R$_{15}$ is H, halo, C$_1$-C$_6$ alkyl, C$_3$-C$_7$ cycloalkyl, aryl, or heteroaryl;
Q is O, S, or NR$_{16}$, where R$_{16}$ is selected from the group consisting of H, C$_1$-C$_6$ alkyl, C$_1$-C$_6$alkyl-C$_3$-C$_9$cycloalkyl, aryl, heteroaryl, arylalkyl, heteroarylalkyl, acyl, and sulfonyl; and
A$_1$ is 1, 2, or 3 substituents which are independently H, C$_1$-C$_6$ alkyl, —OR$_{12}$, halo, alkylamino, aminoalkyl, or heteroarylalkyl.

13. A metal complex of claim 1 in which [X—Y—Z-M$^{n+}$] has a general formula XIX, XX or XXI:

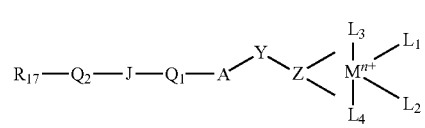
(XIX)

52

-continued

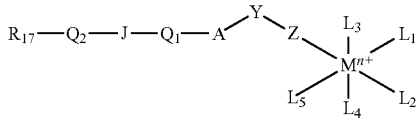
(XX)

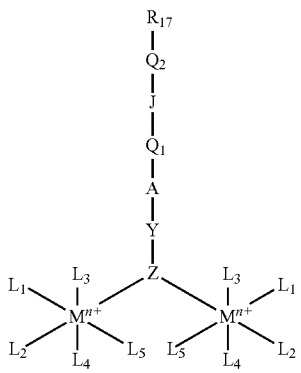
(XXI)

in which:
A is an aryl group;
Q$_1$ is a covalent bond or an aryl leader group;
J is a sulfonamide linkage selected from the group consisting of

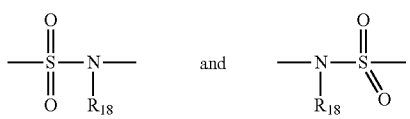

where $R_{18}$ is a sulfonamide substituent;
  $Q_2$ is an acid leader group; and
  $R_{17}$ is a hydroxamate group,
with the proviso that if J is

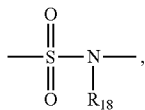

then $Q_1$ is an aryl leader group.

14. A metal complex as claimed in claim 12 in which [X—Y—Z-$M^{n+}$] has a formula:

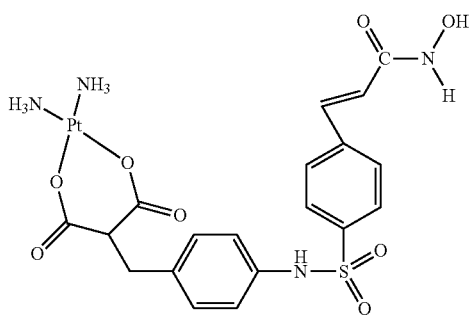

15. An intermediate compound of formula III:

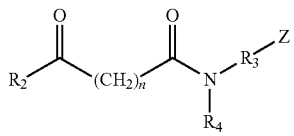

(III)

in which:
  $R_3$—Z is selected from the group consisting of:

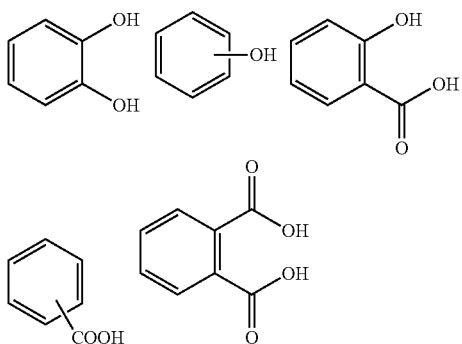

$R_4$ is a hydrogen, hydroxyl, a substituted or unsubstituted, branched or unbranched alkyl, alkenyl, cycloalkyl, aryl, acyl, heteroaryl, arylalkyl, heteroarylalkyl, aryloxy, alkyloxy, arylalkyloxy, aromatic polycycles, non-aromatic polycycles, mixed aryl and non-aryl polycycles, polyheteroaryl, non-aromatic polyheterocycles, or mixed aryl and non-aryl polyheterocycles;

$R_2$ is a hydroxylamino group; and n is an integer from 5 to 8.

16. An intermediate compound as claimed in claim 15 selected from the group consisting of:

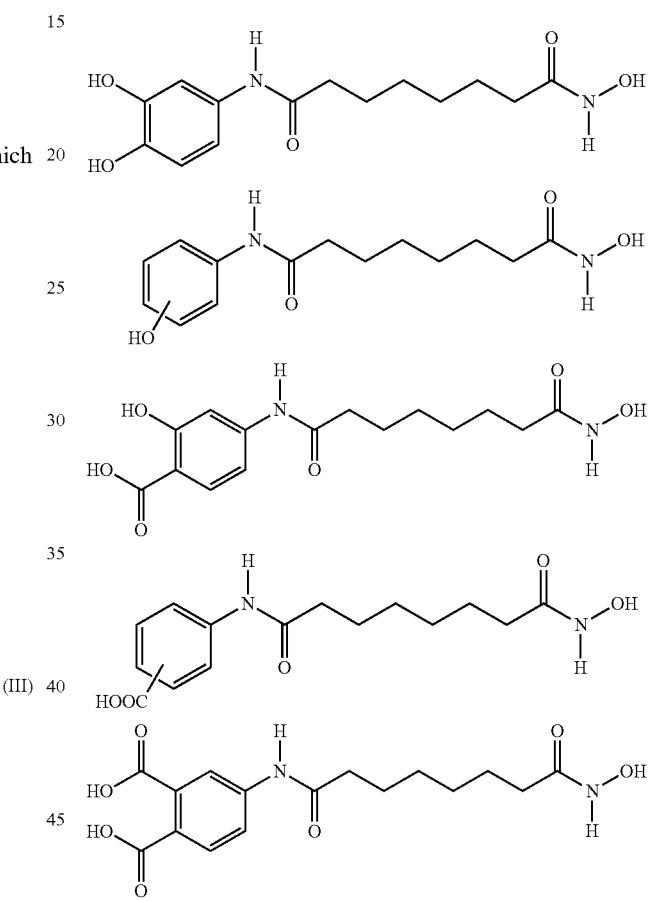

17. A method of forming a metal complex of the type comprising a HDAC inhibitor coordinated to a DNA-binding heavy metal ion, the method comprising the steps of derivatising the HDAC inhibitor with a mono-dentate, bidentate, or chelating, oxygen donor linker group, to provide a monodentate, bidentate, bridging or chelating oxygen donor ligand, and coordinating the DNA-binding heavy metal ion to the monodentate, bidentate, or chelating oxygen donor ligand to provide the metal complex.

\* \* \* \* \*